United States Patent [19]

Elias et al.

[11] Patent Number: 4,638,456
[45] Date of Patent: Jan. 20, 1987

[54] SPOT QUANTITATION

[75] Inventors: John G. Elias, Wilmington; Allan P. Jansson, Hockessin, both of Del.

[73] Assignee: E. I. Du Pont de Nemours and Company, Wilmington, Del.

[21] Appl. No.: 574,712

[22] Filed: Jan. 27, 1984

[51] Int. Cl.$^4$ .......... G06F 15/20; G06K 9/00
[52] U.S. Cl. .................. 364/518; 364/570; 364/525; 364/415; 382/6
[58] Field of Search ........... 364/555, 521, 523, 525, 364/413, 415, 416, 518, 570; 382/6

[56] References Cited

U.S. PATENT DOCUMENTS

| | | | |
|---|---|---|---|
| 3,908,078 | 9/1975 | Auerbach et al. | 364/415 X |
| 4,192,004 | 3/1980 | Buerger | 364/518 X |
| 4,267,573 | 5/1981 | Chaikin et al. | 364/518 X |
| 4,404,683 | 9/1983 | Kobayashi et al. | 364/416 X |
| 4,450,530 | 5/1984 | Llinas et al. | 364/413 X |
| 4,455,609 | 6/1984 | Inamura et al. | 364/413 X |
| 4,481,509 | 11/1984 | Sasaki et al. | 364/518 X |
| 4,485,411 | 11/1984 | Yamamoto | 364/518 X |
| 4,522,482 | 6/1985 | Pettigrew et al. | 364/518 X |

OTHER PUBLICATIONS

"Quantitation of Brain Proteins by Computer-Analyzed Two Dimensional Electrophoresis" in Catsimpoolar, N., (Ed.), Electrophoresis, 1978, Lutin, W. A., Kyle, C. F. and Freeman, J. A.

"Implementation and Application of a Method to Quantitate 2-D Electrophoresis", 1983, 4, pp. 82–91—Jansson, P. A.; Grim, L. B.; Elias, J. G.; Bagley, E. A. and Lonberg-Holm, K. K.

Primary Examiner—Edward J. Wise

[57] ABSTRACT

Describes a method and system for improving the ability to quantitate the amount of flux or material in localized collections of such flux or material typically called a "spot". Quantitation of spots using a software algorithm which utilizes reduction volumes for quantitating peaks in a spot image of an electrophoresis gel is disclosed. The operating system includes a laser gel scanner module, a computer module, system peripherals, and analysis software.

18 Claims, 8 Drawing Figures

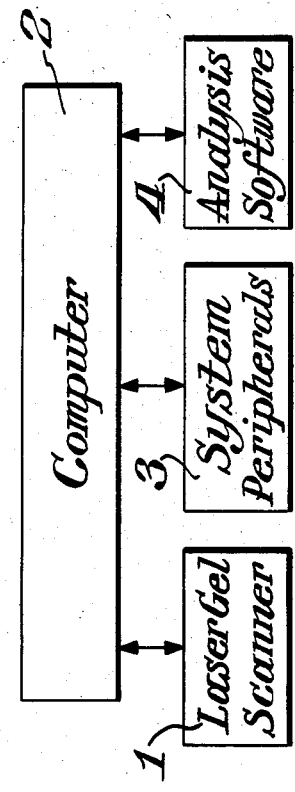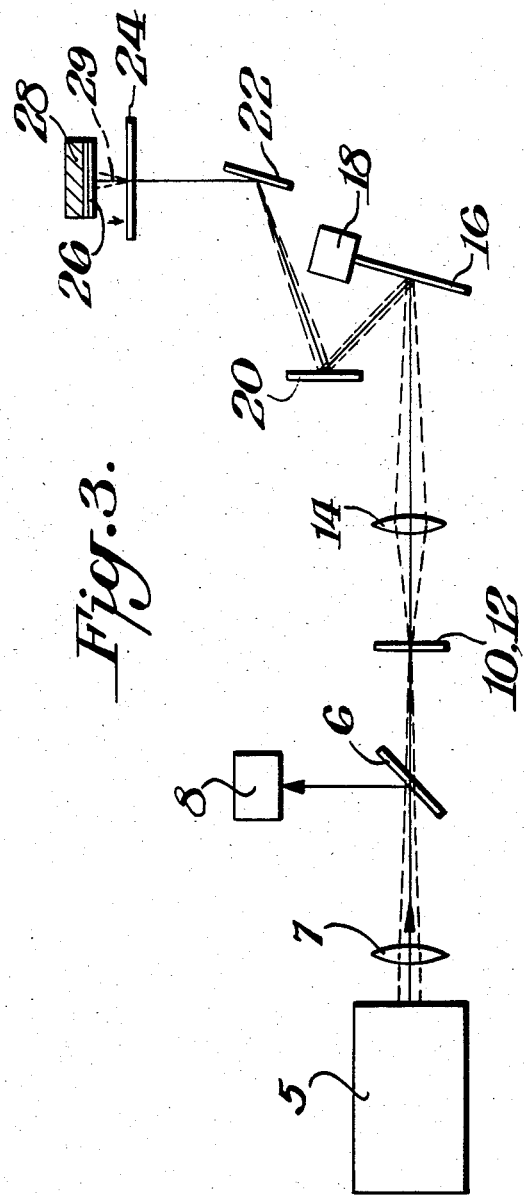

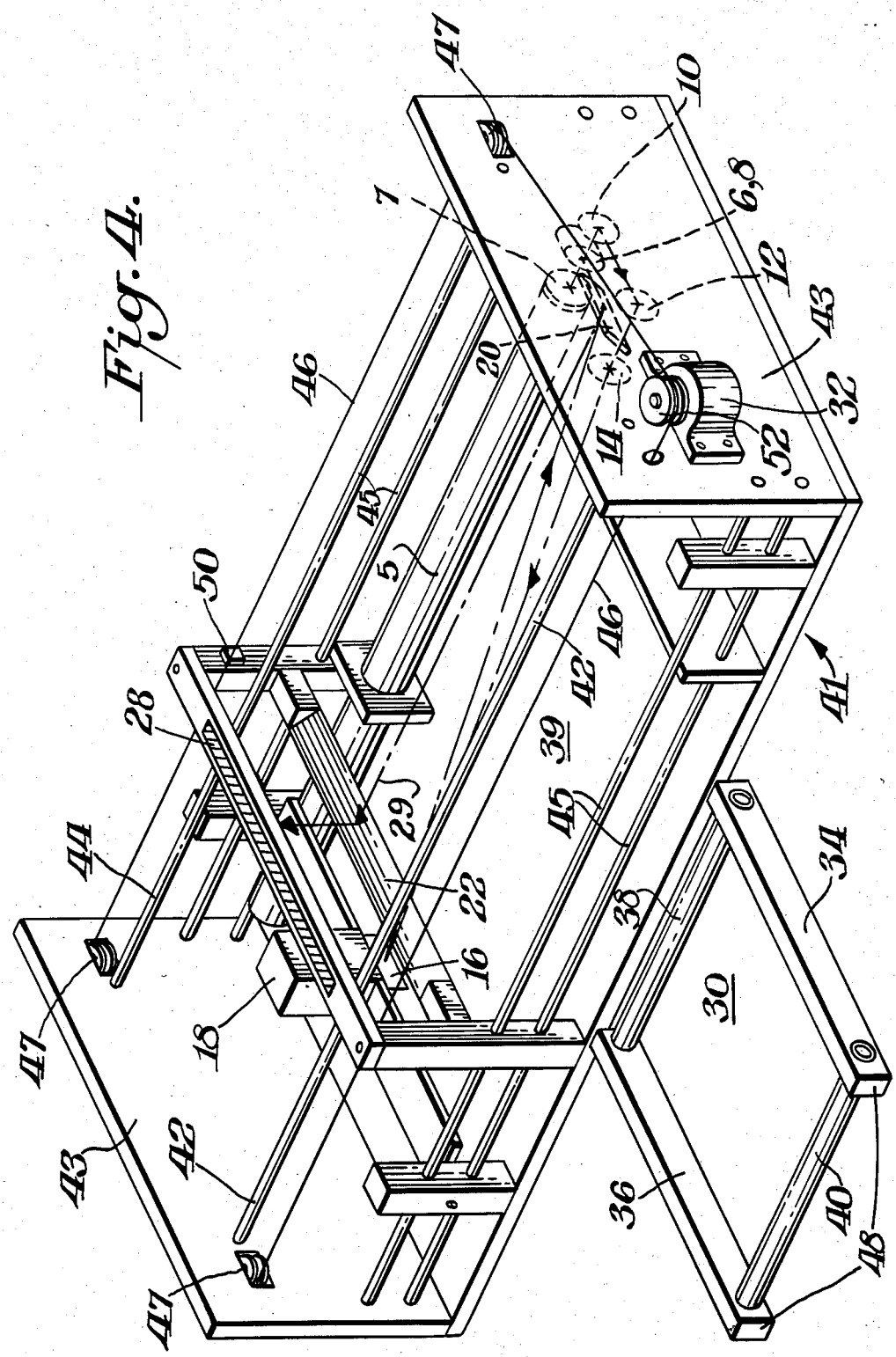

Fig. 7.

IMAGE

Column Number

|   | 1 | 2 | 3 | 4 | 5 | 6 | 7 | 8 |
|---|---|---|---|---|---|---|---|---|
| 1 | 1 | 1 | 1 | 2 | 3 | 5 | 1 | 1 |
| 2 | 1 | 1 | 3 | 5 | 6 | 7 | 5 | 2 |
| 3 | 1 | 2 | 3 | 5 | 6 | 4 | 2 | 1 |
| 4 | 1 | 2 | 2 | 3 | 4 | 3 | 2 | 1 |
| 5 | 1 | 3 | 4 | 3 | 2 | 2 | 1 | 1 |
| 6 | 1 | 3 | 7 | 5 | 3 | 1 | 1 | 0 |
| 7 | 0 | 1 | 4 | 3 | 2 | 1 | 1 | 0 |
| 8 | 1 | 1 | 1 | 2 | 1 | 1 | 1 | 0 |

Row Number

ZMAX TABLE

| Row Number | Maximum | Column Location of Maximum |
|---|---|---|
| 1 | 5 | 6 |
| 2 | 7 | 6 |
| 3 | 6 | 5 |
| 4 | 4 | 5 |
| 5 | 4 | 3 |
| 6 | 7 | 3 |
| 7 | 4 | 3 |
| 8 | 2 | 4 |

SPOT QUANTITATION

CROSS REFERENCE TO RELATED PATENT APPLICATIONS

The invention described herein relates to an invention described in copending application entitled Spot Quantitation, Ser. No. 574,713, filed Jan. 27, 1984.

BACKGROUND OF THE INVENTION

This invention relates to a method and system for improving the ability to quantitate the amount of flux or material in localized collections of such flux or material typically called a "spot". These spots, encountered in such fields as astronomy, chemistry, biology, and the like, may be distributed in patterns, constellations or other configurations. The problems are essentially the same in all of these fields—each spot must be located, resolved from possible overlapping spots and quantitated.

In the area of biotechnology, recent advances in separation technology, in particular two-dimensional gel electrophoresis, have made it possible to separate large numbers of different components that may be present in a complex protein mixture. Typically the separation is carried out on the basis of molecular charge in one dimension and molecular weight in the other. Protein spots thus separated may be stained and viewed directly. Scientists have estimated that 30,000 to 50,000 human-protein gene products may exist. In identifying a given protein after electrophoresis-gel separation, the researcher identifies spots of interest by their known placement in the characteristic overall spot pattern. Quantities of protein are typically judged in a subjective fashion that is not quantitatively accurate. Visual analysis of high resolution gels is laborious and time-consuming owing to the large number of spots that may be present, some of them barely visible. It is easy to overlook changes in the pattern that may be important. Furthermore, accurate determination of the amount of protein present in certain spots is necessary for a number of experiments, including longitudinal studies of clinical patients, and the kinetics of blood chemistry.

In order to improve upon the efficiency and precision by which a spot is analyzed, scientists have utilized automated gel quantitation systems incorporating computers to process the spot pattern images. Several analysis methods that have been used with 2-D gels work well with isolated spots, but are unable to accurately allocate protein between two spots that show overlap. Although a number of the spots on a typical gel are relatively free of overlap with neighbors, enough spots show overlap to make resolvability a very important consideration.

A typical gel quantitation system has four principal components: scanner, software, computer and display. A scanner, typical transmissively or reflectively, converts the image into an array of numerical gray level measurements usually termed pixels, each pixel representing an element of the array, suitable for computer manipulation.

The spots or pixels are obtained in several different ways. For example, the proteins to be separated may be radiolabeled. The radiation flux from these proteins after separation may be used to expose photographic film, thereby forming an autoradiogram of the gel. Or, the proteins may be stained by an optically absorbing material after separation. By either method, a pattern of optically absorbing spots is produced that may be measured with the aid of a scanner or scanning densitometer. The output of such a scanner is typically a series of measurements of the optical density of the stained gel or autoradiogram sample, these measurements being regularly spaced in a rectangular array that covers substantially the entire surface of the sample. The software is a collection of computer programs deisgned to analyze the data supplied by the scanner. The computer analyzes the pixel data by executing the instructions provided by the software. A display system demonstrates the results of this analysis, and permits the user convenient interaction with data and results if necessary.

Many improvements have been made in scanners, computers, and display systems to help quantitate spots, but the area that needs more attention is the quantitation of the spots. A spot can be considered to be a three-dimensional mountain peak with peak height corresponding to maximum spot density, i.e., quantity of protein, surrounded by neighboring peaks of varying width and amplitude. In the prior art there are two general approaches used to quantitate spots. The first approach deals with simple segmentation and contour following; the second approach deals with modeling. Of the two approaches, only modeling can adequately resolve overlapping spots.

A paper by Lutin, W. A., Kyle, C. F. and Freeman, J. A., "Quantitation of Brain Proteins by Computer-Analyzed Two Dimensional Electrophoresis", in Catsimpoolas, N, (Ed.), *Electrophoresis '78*, (Elsevier North Holland, N.Y. 1979), pp. 93-106, describes one such modeling approach. As taught by Lutin et al., the raw scanner data are acquired in the form of pixels or numbers representing the gray level intensity of the spots. These pixels are then processed by the computer to determine which levels of intensity represent the background values. The background pixels are fitted by least squares to a two-dimensional polynominal. The image is then corrected for background variation by subtracting the polynominal value at each pixel location. In addition, the corrected image is smoothed by convolution.

The corrected data now are searched for a maximum value, the tacit assumption being that this value must be at the approximate center of a peak. Once the peak center has been found, inflection points of the peak are sought by scanning the data in all four raster directions away from the maximum found.

The average height of the four inflection points relative to the peak height is compared to that expected for a true gaussian. If a serious discrepancy is noted, the peak is assumed to be subject to interference from a neighboring peak and a Gaussian estimate is made from the inflection point value and maximum values obtained. Inflection points not lying in a plane, or an inflection point plane that is significantly tilted, are also indications that an estimate is necessary. If, on the other hand, the inflection points are those expected for a single isolated gaussian, a weighted least-squares Gaussian fit is performed over the two-dimensional region bounded by the inflection points in order to obtain the Gaussian parameters.

The Gaussian parameters, whether obtained by estimation or fitting, are then used to create a gaussian that is subtracted from the surface. The data are searched again for a maximum. The previously found maximum is, of course, no longer present so a new peak is located. This procedure is continued until the maximum found is below a preset threshold level. When this occurs, the first gaussian is regenerated from its parameters, which have been stored in a list. This gaussian is then added to the surface. Inflection points are tested as before, and the gaussian is either fitted or estimated, then subtracted again. This time, however, the gaussian is found to be less influenced by neighboring peaks, the largest ones have already been removed, at least to a good approximation. The fit or estimate is thus more likely to be accurate. By this means, one is able to obtain good fits while treating only one gaussian at a time. The process is repeated for all gaussians already on the parameter list. After the last gaussian is processed, additional image maxima are determined. Additional gaussians are thus found and subtracted until a lower threshold is reached. Three such passes are made through the list. Each time, the threshold is lowered according to a predetermined sequence of values. After the third pass, a fourth and final pass is made in which estimation is not allowed and a least squares fit is forced for all gaussians.

Although this algorithm is an improvement over the prior art, it requires multiple passes to complete the process, each gaussian being treated several times. This excessive computation results in overall loss of efficiency. In addition, the prior art does not address the problem of negative residuals. These negative residuals are a result of subtracting a Gaussian model whose value in places exceeds the value of the data being modeled. The appearance of a negative residual is an indication that the parameters that were estimated or fitted to the actual peak represent a larger volume than is actually present. In other words, the values used to describe the spot (peak) are in error. Other problems with the prior art include numerical failures that occur when the matrix derived from the least-square normal equations becomes ill-conditioned.

An improved approach to quantitating spots is described in a paper by Jansson, P. A., Grim, L. B., Elias, J. G., Bagley, E. A. and Lonberg-Holm, K. K., "Implementation and Application of a Method to Quantitate 2-D Gel Electrophoresis Patterns" *Electrophoresis* 1983, 4, pp. 82–91, in which the analysis achieves greater stability. Jansson, et al., felt that one aspect of the prior art that needed adaptation was the cut-off criterion. This is the pre-determined density at which the algorithm specifies that peak subtraction is to stop, and peak addition, refitting and re-subtraction is to begin. This process is repeated until a new and lower cutoff is reached. Jansson, et al., noted that the arbitary cutoff previously employed was too high, so that weak spots would be missed. At other times it was too low, so that large numbers of minute gaussians were fitted to noise. The solutions to this problem was the introduction of a mathematical expression that specified this cut-off point by referring to known background parameters. This modification, although it yields an improvement in time efficiency, still does not address the problem of negative residuals, which introduce error in the quantitation of a protein spot. Also, this system is still iterative, utilizing multiple passes to treat each gaussian which is, in turn, time-consuming. This time burden can be relieved by the use of large main-frame computers. The use of these computers is, however, undesirable due to expense and lack of convenience.

SUMMARY OF THE INVENTION

This invention directly addresses the problems of accuracy, time efficiency and expense by an improved spot quantitation method and system. According to the method of this invention, spatially integrated intensities of individual spots are quantitated. The spots are contained in a multiple spot image defined by a discrete pixel-by-pixel representation of the intensities, which establishes a first sense, of the spots. Quantitation of these spots is accomplished by, (a) searching the image for the pixel representing the greatest intensity deviation in the first sense from a reference intensity level, (b) constructing a mathematical three-dimensional model of the spot containing such pixel, (c) compensating the image by substracting the mathematical model therefrom leaving possible overcompensated regions in the image, which regions together constitute a reduction volume, (d) adjusting the dimensions of the model by the amount necessary to give the model the same volume as the volume removed from the image in step (c) less the reduction volume, (e) restoring all such overcompensated regions to the reference intensity level, (f) quantitating the spot from the adjusted model and (g) repeating steps (a) through (f) for successive pixels each having a lower intensity deviation from the reference level until the image is of substantially constant intensity.

The model of step (b) is partially defined by searching the image in four orthogonal directions from the greatest deviation pixel to ascertain the extent of the spot along each direction. Models formed in step (b) of adjacent pixels are combined to form composite models of each individual spot.

The method includes the additional steps of quantitating the spot to obtain its center of mass, adjusting the location of the model for the step (a) pixel according to the alteration of the center of mass caused by the removal of the reduction volume.

The invention is also a system for quantitating individual spots contained in a multiple spot image defined by a discrete pixel-by-pixel representation of the intensity of the spots, the system including a memory for storing the pixels, means for determining that pixel representing the greatest intensity deviation from a reference intensity level, and means for constructing a mathematical three-dimensional model of the spot containing such pixel.

This system is improved in accordance with this invention by compensating the image by subtracting the mathematical model therefrom leaving possible overcompensated regions in the stored image which regions together constitute a reduction volume, adjusting the dimensions of the model by the amount necessary to give the model the same volume as the volume removed from the image in step (c) less the reduction volume, restoring all such overcompensated regions to the reference intensity level and for quantitating the spot from the adjusted model.

BRIEF DESCRIPTION OF THE DRAWINGS

The detailed operation of the method and system described briefly above can be best understood by reference to the following drawings in which:

FIG. 1 is a block diagram of a two-dimensional-Gel Analysis instrument constructed in accordance with this invention;

FIG. 3 is a drawing illustrating the laser beam focusing and directing optics used in the gel scanner of FIG. 1;

FIG. 4 is a pictorial illustration of the scanner mechanical assembly;

FIG. 7 illustrates the use of a max table, which enhances the efficiency of the method.

SYMBOLS

Figure 2:
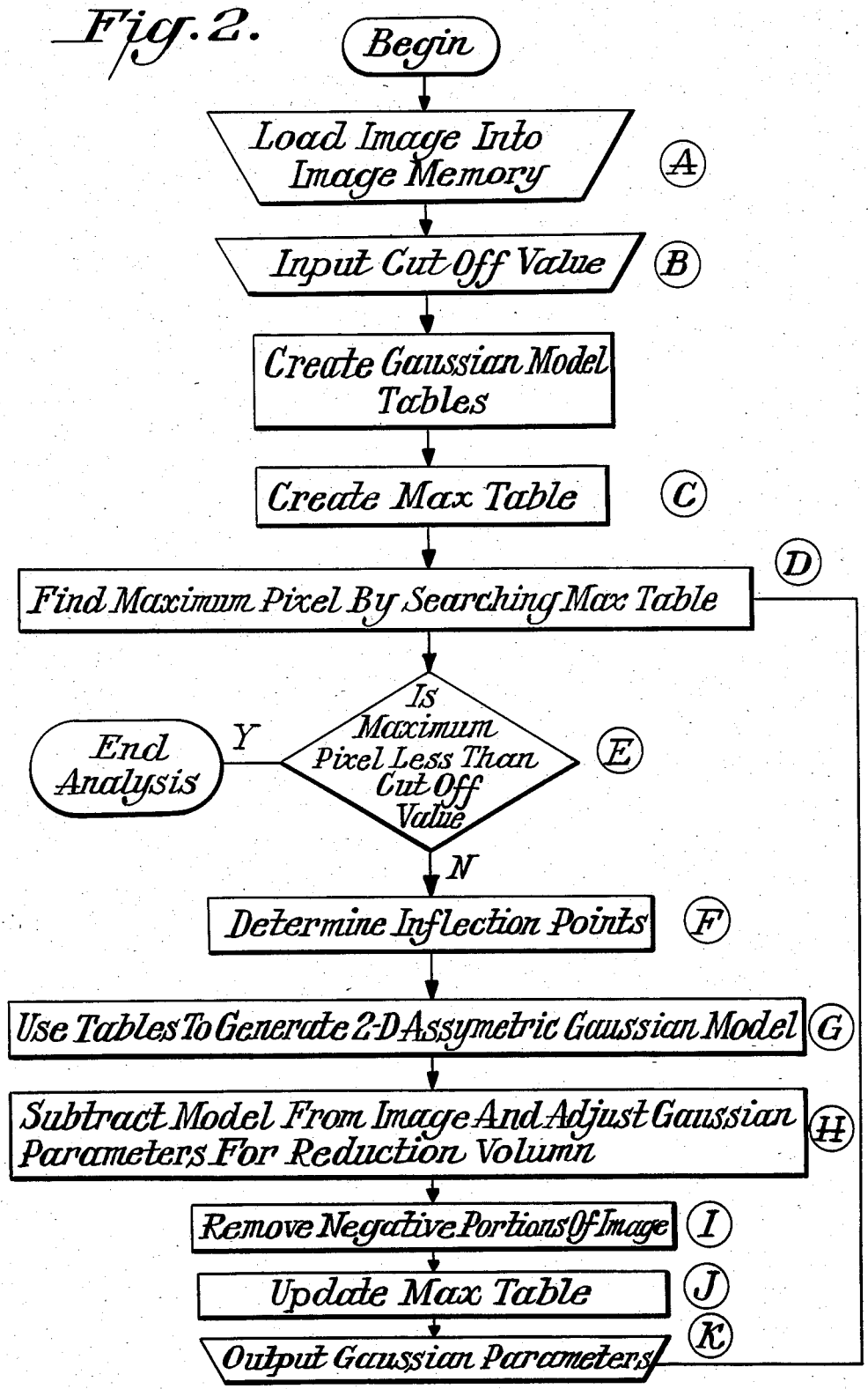
FIG. 2 is a flow diagram describing the manner in which spot patterns are automatically quantitated in accordance with this invention.

The following is a table of symbols that defines the mathematical parameters used throughout the disclosure for convenience of the reader.

| Symbol | Description |
| --- | --- |
| $z(x,y)$ | Intensity samples of image. |
| $z_M(x,y)$ | Assymetric Gaussian model. |
| $V_M$ | Volume of model. |
| $V_R$ | Volume bounded by image $z(x,y)$ after model subtraction and the zero reference plane. |
| $V_A$ | Volume of adjusted model. |
| $\bar{x}, \bar{y}$ | Cartesian coordinates of the center of mass of the positive portion of the image removed; coordinates of the adjusted model center of mass. |
| $x, y$ | Cartesian coordinates in gel image plane. |
| $x_o, y_o$ | Coordinates of center of model; coordinates of maximum pixel. |
| $A$ | Amplitude of Gaussian model; value of maximum pixel. |
| $I_{Rx}, I_{Ry}$ | Moments of inertia of negative (over compensated) region. |
| $I_x, I_y$ | Moments of inertia of unadjusted 4-component gaussian. |
| $\sigma_{x+}, \sigma_{x-}, \sigma_{y+}, \sigma_{y-}$ | Principal inflection point distances from the maximum pixel. |
| $\bar{x}_M, \bar{y}_M$ | Cartesian coordinates of the model center of mass. |
| $\bar{x}_R, \bar{y}_R$ | Cartesian coordinates of negative (over compensated) region. |
| $\sigma_{xM}^2, \sigma_{yM}^2$ | Variances of a 4-component Gaussian model about it's center of mass. |
| $I_{CMx}, I_{CMy}$ | Moments of inertia of adjusted Model about its center of mass. |
| $x_{CM}, y_{CM}$ | Cartesian coordinates of adjusted model center of mass. |
| $\sigma_x^2, \sigma_y^2$ | Variances of adjusted model. |
| $V_A$ | Volume of spot comprising N gaussian. |
| $\bar{x}_{CM}, \bar{y}_{CM}$ | Center of mass of spot comprising N-gaussians |
| $\bar{\sigma}_x, \bar{\sigma}_y$ | Standard deviation of spot comprising N-gaussians. |

DETAILED DESCRIPTION OF THE PREFERRED EMBODIMENT

Overview of the System

Referring to FIG. 1, there is seen a system that may be used to quantitate spots used in performing the method of this invention. The system is described in one of its applications, i.e., quantitating the spots of an electrophoresis gel. It is to be understood, however, that the method and system are equally appliable to quantitating other spot patterns as well, i.e., those encountered in astronomy, as well as in chemistry and biology. Although the method and system of this invention relate to the quantitation of the spots in a spot image, in order to provide a complete disclose of an operative system, a gel scanning system that has been successfully built and operated to scan a spot image and provide a pixel-by-pixel representation thereof is described.

The system includes a laser gel scanner module 1, a computer module 2, system peripherals 3, and analysis software 4. The laser gel scanner 1 digitizes, with high resolution, the two-dimensional optical-density information in 2-D electrophoresis gels. The computer system 2 serves many functions. It transmits the scan parameters to the laser scanner's control circuitry. It assists in the transfer of data from the scanner to an image memory. It processes the image data according to specially designed algorithms. And, it helps to effect data movement from various storage systems to a video display device. The system peripherals include a CRT terminal, color monitor, printer and floppy disk drive and hard disk drive.

I. METHOD OF THE INVENTION

The method of this invention, which overcomes may of the difficulties experienced in the prior art, is a one-pass method that treats each spot or peak once. After each spot has been modeled and the model subtracted from the image, the resultant model's parameters are stored and not accessed again until it is time to combine the individual resultant models into spot structures.

Figure 6:
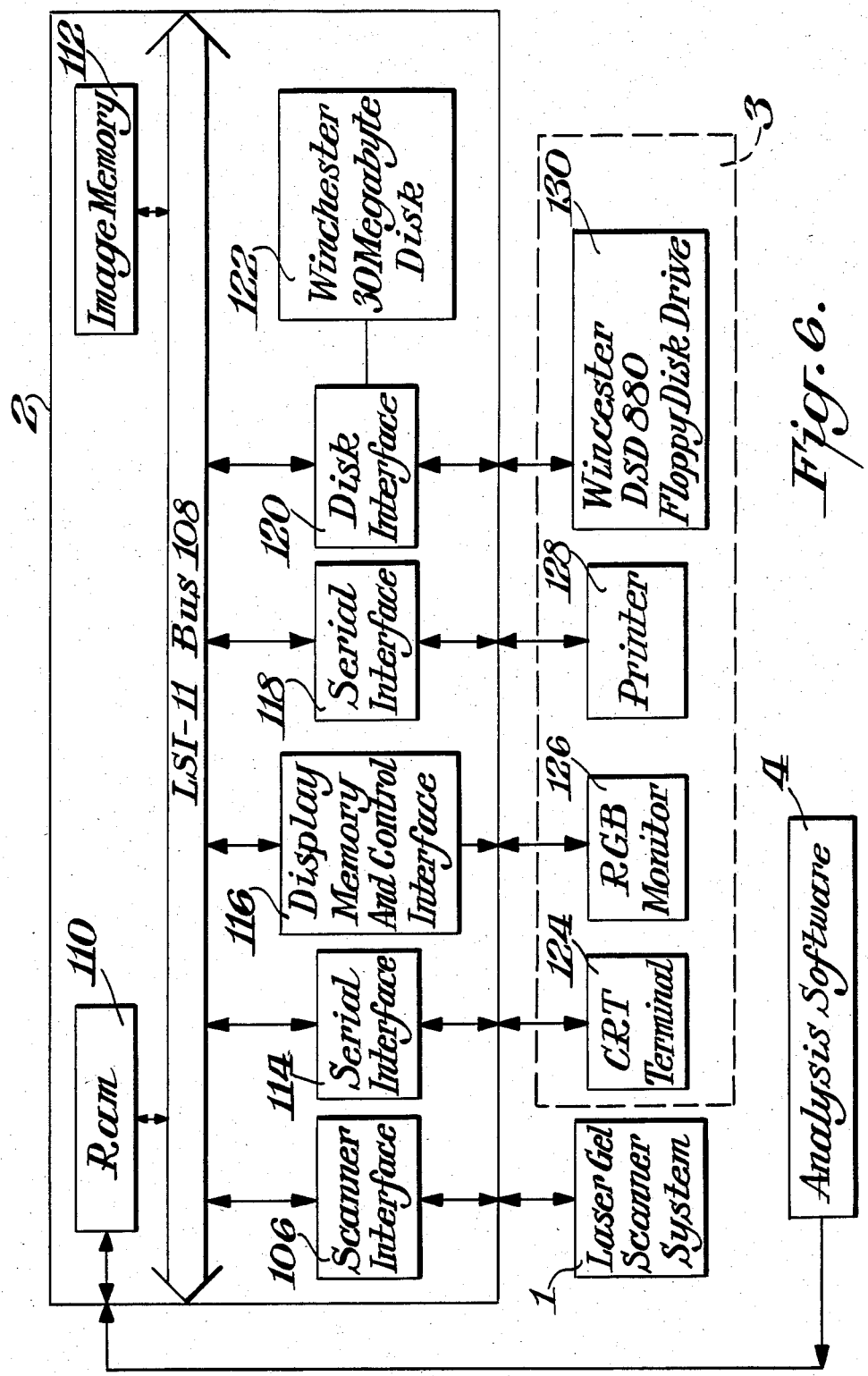
FIG. 6 is a block diagram of the computer depicted in FIG. 1.

The method begins by loading the individual array of elements or a pixels defining the image from the scanner, disk, or other storage medium into the image random access memory 110 (FIG. 6). The image is then pre-processed using known techniques, such as described by Lutin et al., so as to render the background substantially zero, and the volumes to be measured as positive quantities. The value of a positive cutoff level is entered. This level represents a surface close to a background reference level of the image. When all of the image, outside the region between this level and the reference level has been modeled, the initial modeling step is completed. It is to be understood that, in its most general form, the method of this invention can deal with both positive and negative images, and with varying backgrounds.

Next the value of the maximum intensity pixel in the image is sought. In the following description the optical density samples of the image i.e., pixels will be represented by integer values of $z(x,y)$ where x and y are cartesian coordinates in the image plane represented as integers.

Hence if the maximum is greater than the preselected cutoff value, the image is searched, starting at the peak pixel position in the four principal orthogonal cartesian coordinate directions to ascertain the extent of the spot. This extent may differ in all four directions. Once the extent has been determined, an appropriate model is generated and subtracted from the data. Because of the differing extent measurements, the most accurate model needs to be assymetric. Because the model is approximate, over-compensation for the image data may occur in certain regions, i.e., the model value may exceed the surface $z(x,y)$ at certain pixels, resulting in a negative residual in the image array. If the model parameters that are to be stored on a parameter list are to accurately represent the volume under the original surface $z(x,y)$, they must be adjusted so that the model volume equals the volume under the positive $z(x,y)$ that was removed. Model extent and/or position parameters are adjusted accordingly.

By an analogy drawn from mechanics, unique model-width parameters are established that incorporate information from all pixels processed. Note that spatial position information concerning every element of mass in a solid body is used in determining the bodies center of mass and moment of inertia properties. By considering the spots as if they were solid bodies, it is apparent that these properties are candidates for spot position and shape measures. The parallel axis theorem provides an elegant method of combining the moments of inertia of separate components of a composite model. More conventional width measures are then more easily obtained from the composite moments. The parallel axis theorem is used to establish these parameters. The incorporation of all information stands in contrast to the original use of inflection points, which only included information along a swath parallel to each cartesian coordinate axis and passing through the maximum pixel. The virtue of the new parameters for volume, position, and width or extent is that they can be combined in a sensible way in subsequent steps to yield parameters of composite, multi-model spot structures such as would be obtained by direct calculation from the original image data.

After the parameters are adjusted, negative portions of the image are removed and the parameters are added to a list. The next maximum of the image, which has been adjusted as just described, is then sought in a repetition of previous steps as indicated in FIG. 2. With each successive subtraction, the maximum found decreases, until it is less than the cutoff value and the method terminates. At this point, the total volume under the models represented on the parameter list substantially equals the original volume under the surface $z(x,y)$ and we say that $z(x,y)$ has been adequately parameterized.

In subsequent steps the model volume center coordinates and widths are combined to form single spot composite structures that are characterized by like parameters. It is a property of the analogy with mechanics, i.e., the use of center of mass, and moments of inertia, that allows the combination of all these parameters in a way that results in values that are the same as one would obtain if one computed the parameters directly by their definition from the spot image data alone. The latter technique, however, only works for isolated spots. This method and system has the significant advantage of being able to resolve overlapping spots.

High-resolution 2-D gel-separation technology is believed to offer a key element needed to understand the structure and function of the molecular building blocks underlying life itself. This understanding will lead to improvement in the quality of life through the treatment of disease and alleviation of suffering. The technology of 2-D gel-separation cannot reach its potential without practical methods of spot quantitation.

At present, there are basically two classes of spot quantitation methods:

Modeling methods—spot resolving but inefficient.

Segmentation methods and related types—potentially efficient but non-resolving.

Efficiency and resolving capability are of paramount importance. Spot resolving capability is needed because a significant number of spots on a typical gel overlap. A method that cannot resolve them is limited in applicability. Efficiency is needed because inefficient programs require either long execution times, large expensive computers, expensive array processing hardware, or all of the above. Any of these requirements would make a method impractical for widespread use. The invention disclosed here combines the best features of both classes of methods, namely efficiency and resolving capability.

It is therefore, believed to hold the key to widespread adoption of not only computerized gel quantitation, but 2-D gel separation technology itself.

METHOD DETAILS

While the method and apparatus of the invention can be used in the quantitation of the spot-like representations of many types such as thin layer chromatograms, radio maps of the sky, or astronomical plates, it is herein described as being used for the quantitation of spots on 2-D electrophoresis gels. The gel optical densities are digitized by the scanner (as will be described) to a desired precision (typically 1 part in 256, ie., 8-Bit encoding is adequate) over an image format of selected density. Typically a 1024×1024 pixel array is satisfactory, although higher densities such as 2048×2048 pixel array may be used merely by the addition of memory.

In the following discussion the reader will wish to refer to the Flow Chart of FIG. 2.

Also, the digital data are corrected to render the spots as positive-going peaks superimposed on a zero-level background. Finally the scanned, corrected spots are stored as an array in a random access memory in a manner that is well known in the art. A cutoff value is then either read from disk or entered by an operator. The cutoff value is chosen to represent a positive value or surface close to zero such that when all volume outside the region between this surface and zero is accounted for by models represented on the parameter list, the gel is considered to be adequately quantitated. As stated previously, the mathematical model used may be any model that represents a localized, bounded volume. An assymetric 4-component gaussian is preferred, although certain other assymetric models should probably work nearly as well.

To speed later computation of the model, exponential and square-function look-up tables are generated and stored at this point in the program for future reference. Because later searching for maxima would otherwise be a time-consuming step, next the image is searched to generate a max table in which the largest valued pixel of each image row or column is located and stored. The properties of the max table are detailed in a later section. From the max table, the pixel having the largest value in the entire array is located. If the maximum is greater than or equal to the cutoff value previously selected, which it certainly should be on this time through the loop, the program goes on to determine the extent of the model. After the algorithm has run for a while, a similarly located maximum pixel will fall below cutoff and the analysis will terminate.

When using an assymetric gaussian as the model, the inflection points of the data are especially convenient as descriptors of extent of each spot. This arises from the fact that, for a Gaussian function, the inflection point occurs precisely one standard deviation from the peak. Thus we obtain four inflection points and generate the mathematical model as will be described. The model is subtracted from the image and the Gaussian parameters are adjusted to account for any negative-going overcompensated regions of the image. This, too, will be described in detail under a following heading. The negative portions of the image are zeroed, and the max table is updated so that it will contain the most current pixel maxima in the image rows affected by the above described modeling. The parameters of the model, adjusted for negative-going regions, are placed on a list that may reside on a disk. The max table is then searched for the next maximum. As noted previously, the algorithm terminates when the maximum found is below cutoff.

Next, the various individual models represented by the parameters stored on the parameter list may be combined in appropriate groups representing single spot structures. The method by which these models are combined is generally that described in the prior art by Jansson et al. with several improvements. It is a unique property of the Gaussian parameters $V_A$, $\sigma_x$, $\sigma_y$, $\bar{x}$, and $\bar{y}$ that they may be easily combined in a sensible way to form overall spot volumes, width parameters and center-of-mass coordinates. The virtue of this technique, however, lies in its efficiency and applicability to overlapping spots. Its utility stems from the frequent occurence of such overlapping spots, and the lack of any other efficient method to sensibly allocated volumes between the spots, accurately determine their positions, and accurately determine their width parameters.

While the method described above executes more efficiently than any other resolving method, the speed can be further improved by eliminating the calculation for $\sigma_x^2$ and $\sigma_y^2$. The improvement is chiefly a result of eliminating a summation employed in computing $I_{Rx}$ and $I_{Ry}$. The principal utility of the parameters obtained is in the recognition of spots by virtue of the shape information thus conveyed. If the analyst is only interested in quantitation of integrated spot density, the faster computation method is preferable. In appendix 1 there is set forth FORTRAN and assembly language programs and subroutines that together constitute the details of the faster method.

The Max Table

In the original Lutin et al. method, and in the simplest version of the present method, the most computer time consuming step is searching the entire image for the maximum pixel. In the case of a $1024 \times 1024$ pixel image, some $1024^2 = 1,048,576$ pixels need to be tested each time through the loop. To alleviate this problem, a max table that records the maximum pixel in each row of the image, and its position in the row is used (FIG. 7).

The table is initialized by a complete search of the image (FIG. 2, Step C) before any model subtractions have been done. Each time a new maximum value is needed, the image maximum is found merely by seeking the largest value in the maximum column of the max table. The numbers adjacent to the largest value in the max table specify the row and column containing the maximum pixel. For a $1024 \times 1024$ image, only 1024 values in the max table need to be checked, a reduction by a factor of 1024 times in the computation needed for seeking the maximum.

In order that the max table accurately represent the values in the image, it must be updated every time the image values are altered, that is, every time a mathematical model such as a gaussian is subtracted in Step H, new maximum values and column location values must be placed in the max table in step J for all rows affected in step H.

DETERMINING THE INFLECTION POINTS

When the image maximum has been located (Step D), the closest inflection points to this maximum in each of the four principal orthogonal coordinate directions are sought; that is, the first inflection points in the $+x$, $-x$, $+y$, and $-y$ directions. Thus far the determination of inflection points is usually done by finding the pixel location where the second partial derivative vanishes. This approach is similar to that taken in the prior art. A finite difference technique is appropriate. Because of the well known propensity for differentiation to emphasize the effects of high-frequency noise in the data, the technique is prone to inaccuracies resulting in the establishment of erroneous locations for the inflection points.

To partially overcome this problem, each pixel along one of the four principal coordinate directions is replaced (for the purpose of inflection-point finding only) by the average of itself and its 6 closest neighbors along a line perpendicular to the principal direction in which the inflection point is sought. This too is described in the prior art. Even this averaging is not sufficient, however, so the prior art stresses the need to filter the entire image before analysis by convolving it with a smoothing function. Unfortunately, these techniques taught by Lutin et al., are a time-consuming procedure.

Overall filtering is avoided by using a method that makes use of the information in neighboring points along the principal direction in which the inflection point is sought. This stands in contrast to the prior art, in which only neighbors perpendicular to the principal direction are employed. Thus, when the inflection point is sought along the principal direction whose pixels have been replaced by averages as noted above, the inflection points are obtained by calculating the second derivative through use of a well known method of simplified least squares. This method is described by Savitzky, A. and Golay, M. J. E., *Analytical Chemistry*, Vol. 36, No. 8, pg, 1627–1629, July 1964. This method makes use of the information in neighboring pixels along the principal direction as well as the information perpendicular to the principal direction, as was described in the prior art.

In practice, inflection points calculated as above do not generally occur at exact pixel locations, i.e., integer values of distance from the maximum point. Therefore, the non-integer inflection points distances used for subsequent modeling are rounded up to the next largest integer.

TWO-DIMENSIONAL ASSYMETRIC GAUSSIAN MODEL

While any model having a shape that localizes a volume may be used in the present algorithm, it is convenient to employ a Gaussian function of the two independent gel-plane coordinates. However, inflection points need not be, and usually are not, at equal distances from the maximum pixel; that is, the $+x$ and $-x$ distances are not equal and the $+y$ and $-y$ distances are not equal. These differences are a natural consequence of the assymetric shape that protein spots typically have. This information is retained by this invention.

Accordingly, this invention employs an assymetric volume model having four characteristic spatial dimensions. In the preferred embodiment, each cartesian quadrant of the Gaussian function is identical to a quadrant of the function described in the prior art (Lutin, et al.). If $\sigma_{x+}$, $\sigma_{x-}$, $\sigma_{y+}$, and $\sigma_{y-}$ are the four principal inflection-point distances from the maximum pixel as noted elsewhere, then the model in this invention is, for the first quadrant, in which both $x - x_o$ and $y - y_o$ are positive, $$Z_M(x,y) =$$

-continued $$A \exp\{-[(x-x_o)/\sigma_{x+}\sqrt{2}]^2\}\exp\{-[(y-y_o)/\sigma_{y+}\sqrt{2}]^2\},$$

for the second quadrant, in which $x-x_o$ is negative and $y-y_o$ is positive, $$z_M(x,y) = A \exp\{-[(x-x_o)/\sigma_{x-}\sqrt{2}]^2\}\exp\{-[(y-y_o)/\sigma_{y+}\sqrt{2}]^2\},$$

for the third quadrant, in which $x-x_o$ and $y-y_o$ are negative, $$z_M(x,y) = A \exp\{-[(x-x_o)/\sigma_{x-}\sqrt{2}]^2\}\exp\{-[(y-y_o)/\sigma_{y-}\sqrt{2}]^2\},$$

and for the fourth quadrant, in which $x-x_o$ is positive and $y-y_o$ is negative, $$z_M(x,y) = A \exp\{-[(x-x_o)/\sigma_{x+}\sqrt{2}]^2\}\exp\{-[(y-y_o)/\sigma_{y-}\sqrt{2}]^2\}.$$

In the above formulas, $z_M(x,y)$ is the value of the model at the pixel located at the gel plane cartesian coordinates x and y, $x_o$ and $y_o$ are the coordinates of the center of the model (which is chosen as the coordinates of the maximum pixel) and A is the amplitude of the model, which is chosen as the value of the maximum pixel.

The volume of the model is easily obtained by summing the volumes of the four components which, in turn, are easily obtained by either direct integration or from a table of integrals. Thus we find:

$$V_M = (\pi A/2)(\sigma_{x+} + \sigma_{x-})(\sigma_{y+} + \sigma_{y-}).$$

Because the Gaussian model falls to a relatively small value within a relatively short distance from its center coordinates of $(x_o, y_o)$, the model is evaluated and subtracted from the image only within a rectangle in which this operation would cause significant alteration of the image. Therefore, computation time is greatly reduced as compared with that which would be required to evaluate the model over the entire image plane. The boundaries of the rectangle may be usefully specified as the vertical straight lines located at $$x = x_o + \sigma_{x+}\sqrt{\ln A} \text{ and } x = x_o - \sigma_{x-}\sqrt{\ln A},$$

and the horizontal straight lines located at $$y = y_o - \sigma_{y-}\sqrt{\ln A} \text{ and } y = y_o + \sigma_{y+}\sqrt{\ln A}.$$

In order to save time, the model is computed with the aid of look-up tables, thereby eliminating repeated computation of the exponential expression for each pixel in each model. In the method of this invention, the tables are established before beginning the analysis. The two principal computations that are time-consuming in generating the model are the exponential function and the square operation, so two tables are employed.

SUBTRACTING THE MODEL AND ADJUSTING THE PARAMETERS

When the model is subtracted from the image surface, negative regions result that represent overcompensation for the image values. This effect occurs at all pixel locations at which the values of the model $z_M(x,y)$ exceed the value of the pixel $z(x,y)$. As subtraction is carried out at each pixel, the image is updated by replacing each image value $z(x,y)$ by $z(x,y) - z_M(x,y)$.

In accordance with this invention the total volume between the negative regions and the zero reference plane $V_R$ may be compensated by forming the sum $$V_R = - \sum_{\substack{x,y \\ \text{for} \\ z<0}} z(x,y).$$

The true volume of the positive image data removed by the subtraction process (hence the true volume of protein removed by modeling, in the case of two-D gel electrophoresis) is easily obtained as the adjusted volume.

$$V_A = V_M - V_R.$$

Because it is necessary to record and eventually further process the data, it is often useful to adjust other Gaussian parameters as a function of the adjusted volume. For example, the amplitude A may be adjusted so that a 4-compound gaussian having widths $\sigma_{x+}$, $\sigma_{x-}$, $\sigma_{y+}$, $\sigma_{y-}$ and adjusted amplitude would have the adjusted volume $V_A$. Alternately, all the parameters, including both A and $\sigma$'s might be reduced to achieve the same end. Two questions are thus presented: (1) What should be considered to be the center of the adjusted model? and (2) How does one characterize its width in a simple way such that when multiple models are later combined into single spot entities, the width parameters retain a sensible meaning?

This problem is solved in accordance with this invention by an analogy to the dynamics of rotating bodies, particularly the physical properties that are used in characterizing their motion.

To determine the center of a spot, this spot may be considered as if it had mass, of a uniform density within the volume defined by a local peak of $z(x,y)$. One may then obtain the center of mass of the positive portion of the image removed by using the difference of the volume-weighted model center of mass and the volume-weighted negative region's center of mass. That is for the x coordinate, we find that $$\bar{x} = (V_M \bar{x}_M - V_R \bar{x}_R)/(V_M - V_R),$$

where the model center of mass is given by $$\bar{x}_M = x_o + \sqrt{2/\pi}\,(\sigma_{x+} - \sigma_{x-}),$$

and the negative region's center of mass is given by $$\bar{x}_R = \sum_{z<0} x\,z(x,y) / \sum_{z<0} z(x,y),$$

where the summations are understood to cover all integer values of x and y within the rectangle. Here $z(x,y)$ is taken to be the image after subtraction of the model. By precise analogy, we find for the y coordinate $$\bar{y} = (V_M\bar{y}_M - V_R\bar{y}_R)/(V_M - V_R)$$

where $$\bar{y}_M = y_o + \sqrt{2/\pi}\,(\sigma_{y+} - \sigma_{y-})$$

and $$\bar{y}_R = \sum_{z<0} y\,z(x,y)\bigg/\sum_{z<0} z(x,y).$$

It is known that the moments of inertia of physical bodies can be combined provided that the moments about their respective centers of mass are known, and that the coordinates of the spatial distribution of masses is known. This may be done with the parallel-axis theorem of mechanics. The result of such a combination is a moment of inertia of the aggregate masses about their common center of mass.

The applicability of the analogy becomes clearer when one realizes that the moment of inertia is given by the simple product of the volume and variance $\sigma^2$. (Note that in the case of a perfect gaussian, the variance is the inflection-point distance squared). By knowing the centers of mass of each of the four components of the model and applying the parallel-axis theorem, the aggregate moment of inertia may be determined about the four-component aggregate center of mass. Once that moment is obtained, the variance results by dividing the moment by the aggregate mass. By following this procedure it is easy to derive the variances of a four-component Gaussian model about it's center of mass:

$$\sigma_{xM}^2 = [(1-2/\pi)(\sigma_{x+}^2+\sigma_{x-}^2)+(4/\pi-1)\sigma_{x+}\sigma_{x-}]$$

$$\sigma_{yM}^2 = [(1-2/\pi)(\sigma_{y+}^2+\sigma_{y-}^2)+(4/\pi-1)\sigma_{y+}\sigma_{y-}].$$

Similarly, the variances of the adjusted model are easily obtained by using the parallel-axis theorem to combine the moments of inertia $I_x$, $I_y$ of the unadjusted four-component gaussian and the moments of inertia $I_{Ry}$, $I_{Rx}$ of the negative region. Following this procedure, one finds the variances $\sigma_x^2$ and $\sigma_y^2$ to be $$\sigma_x^2 = I_{CMx}/(V_M - V_R),$$

$$\sigma_y^2 = I_{CMy}/(V_M - V_R),$$

where $I_{CMx}$ and $I_{CMy}$ are given by $$I_{CMx} = (I_x - I_{Rx}) - (V_M - V_R)(x_o - x_{CM})^2,$$

$$I_{CMy} = (I_y - I_{Ry}) - (V_M - V_R)(y_o - y_{CM})^2,$$

$I_x$ and $I_y$ are given by $$I_x = (\pi A/2)(\sigma_{x+} + \sigma_{x-})(\sigma_{x+}^3 + \sigma_{x-}^3),$$

$$I_y = (\pi A/2)(\sigma_{y+} + \sigma_{y-})(\sigma_{y+}^3 + \sigma_{y-}^3),$$

$I_{Rx}$ and $I_{Ry}$ are given by $$I_{Rx} = -\sum_{z<0} z(x,y)(x - x_o)^2$$

$$I_{Ry} = -\sum_{z<0} z(x,y)(y - y_o)^2$$

and $x_{CM}$ and $y_{CM}$, which locate the adjusted model's center of mass, are given by $$x_{CM} = (V_M\bar{x}_M + \sum_{z<0} xz(x,y))/(V_M - V_R)$$

$$y_{CM} = (V_M\bar{y}_M + \sum_{z<0} yz(x,y))/(V_M - V_R)$$

In the above equation, $z(x,y)$ is understood to be the image after subtraction of the model, and the summation is taken to cover the entire region specified by integer values of x and y within the previously described rectangle. Next, as described previously the max table is updated.

PEAK COMBINING

After the modeling algorithm has completed its work and substantially all the integrated optical density (volume) under the surface $z(x,y)$ has been accounted for in the values of $V_A$ stored on the parameters list, the various single models represented by the parameters stored on the parameter list may be combined in appropriate groups representing single spot structures. It is the unique property of the parameters $V_A$, $\sigma_x$, $\sigma_y$, $\bar{x}$ and $\bar{y}$ that they too may be easily combined in a sensible way to form overall spot volumes, width parameters, and center of mass coordinates. The prior art (Jansson et al.) describes the preferred human-interactive peak-combining method of selecting gaussians to be included in the composite model for each spot.

This method employs a digital-refreshed-raster display to represent the models as colored crosses superimposed on the spot pattern image. As the operator selects models to be incorporated into each spot composite, the colors of the crosses are altered to show which model has been selected.

The method presently employed is identical to the prior art except for the following refinement:

(1) The plus-arm lengths determined by the four standard deviations $\sigma_{x+}$, $\sigma_{x-}$, $\sigma_{y+}$, and $\sigma_{y-}$ are now displayed instead of the 1/e points described in the prior art, (2) The console terminal numeric keypad has replaced the joystick as a means of positioning the cursor.

(3) A different display system is being used that, in this instrument, performs the same function as in the system described in the prior art, (4) The standard deviations $\bar{\sigma}_x$ and $\bar{\sigma}_y$ of the spot are computed with the aid of the parallel-axis theorem by referring to the moment-of-inertia analogy employed earlier.

Explicitly, assume that one is given the parameter for N adjusted gaussians where the parameters for the $i^{th}$ adjusted gaussian are expressed as:

$(V_A)_i$, $(x_{CM})_i$, $(y_{CM})_i$, $(\sigma_x)_i$, $(\sigma_y)_i$.

Note: (Parentheses and the subscript i have been added to the notation previously introduced to signify that the parameters correspond to the $i^{th}$ gaussian.)

The parameters for the spot comprising the N gaussians may then be obtained as follows. The volume of the spot is given by $$\overline{V_A} = \sum_i (V_A)_i.$$

The center of mass of the spot is given by $$\overline{x}_{CM} = \sum_i (x_{CM})_i (V_A)_i / \overline{V_A}$$

and $$\overline{y}_{CM} = \sum_i (y_{CM})_i (V_A)_i / \overline{V_A},$$

respectively. The x and y standard deviations of the spot are given by $$\overline{\sigma}_x = \left\{ \left[ \sum_i (V_A)_i \{(\sigma_x)_i^2 + [\overline{x}_{CM} - (x_{CM})_i]^2\} \right] / \sum_i (V_A)_i \right\}^{\frac{1}{2}}$$

and $$\overline{\sigma}_y = \left\{ \left[ \sum_i (V_A)_i \{(\sigma_y)_i^2 + [\overline{y}_{CM} - (y_{CM})_i]^2\} \right] / \sum_i (V_A)_i \right\}^{\frac{1}{2}},$$

respectively. The results obtained by these formulas are the same as those that would have been obtained by computing the volumes, center of mass coordinates, and standard deviations directly from the spot data, for one isolated spot, by use of their respective definitions.

By using the above methods of quantitation and peak combining, however, two substantial advantages are gained:

(1) One is able to correctly characterize spots that are partially overlapping and, (2) Computer-time-consuming explicit summations need only be carried out in regions of overcompensation.

The models account completely for contributions elsewhere. The advantage of applicability to overlapping spots has special significance because of the frequent occurrence of such spots.

The above-described spot parameters result from contributions over the entire spot. They are measures of volume, location, and shape, respectively, that draw upon every optical density measurement in the spot, and are, therefore, truly representative. Because they are integral measures, they exhibit the precision and noise-minimizing properties that are characteristic of averaging processes.

Furthermore, these means are seen to successfully and simultaneously solve the problems of accuracy, precision, efficiency, and resolving capability.

II: LASER GEL SCANNER

The laser gel scanner that has been used successfully to provide the image data processed by this invention will be described in three parts: The beam focusing and directly optics (FIG. 3), the gel scanner mechanical assembly (FIG. 4); and the gel scanner electronics and data interface system (FIG. 5). It is to be understood, however, that any suitable image or radiation scanning system can be used. The subject invention is concerned only with the processing of spot image data to quantitate the spots.

BEAM FOCUSING AND DIRECTING OPTICS

Refering to FIGS. 3 and 4, the laser scanner uses a low powered He-Ne laser 5 as the source of a focused laser beam 29 that is swept rapidly in a transverse direction relative to the line of movement of a gel such that the focal line is adjacent to, but not coincidental with, the gel surface. This is done in order to obtain an optimal beam spot size. In describing the optical train the laser 5, typically a 5 mW He-Ne source, produces a substantially parallel beam 29 which is focused by lens 7 to a point between respective first and second folding mirrors 10, 12. A beam splitter 6 is interposed between lens 4 and first folding mirror 10 to direct a portion of the beam to a reference photodiode 8, which in turn, generates a reference signal input for the optical density analyzer. The laser beam, after being reflected from the second folding mirror 12, passes to a second lens 14, which in turn, brings the beam to a focus at a point near, but not necessarily on, the gel plane 24.

A scan mirror 16, driven by galvo (galvanometer) scanner 18, scans the focused beam across a third and fourth folding mirrors 20, 22 in series and thence to the long-line photodiode sensor 28, typically a 9"×¼" SchottKy photodiode manufactured by United Detector Technology. The third and fourth folding mirrors 20, 22 have been positioned after the scan mirror 16 to lengthen the scan radius sufficiently to maintain (within 2.5 degrees) the perpendicularity of the scan beam to the gel plane 24 throughout the extent of each scan. This is done so as to avoid the effects of apparent changes in optical density in the plane 24 as the scan is generated. As a further measure to enhance the uniformity of response of this detector 28 a strip of opal glass 26 is positioned adjacent to the photosensitive surface to diffuse the light, thereby averaging and minimizing the effect of any nonuniformities that may be present.

If the beam is truly perpendicular to the gel at any beam position, say at the center of the scan, then optical interference may corrupt the data due to the appearance of fringes superimposed on the image. The interference arises because the direct beam and the beam internally reflected in the plate and/or gel are coaxial when the beam is perpendicular. This interference problem is avoided by adjusting the geometry of the beam deflection so that the beam is not perpendicular at any beam position during the scan. This condition is obtained by inclining the beam slightly in the plane that is perpendicular to both the gel plane and the plane that is defined by the beam sweep.

GEL SCANNER MECHANICAL ASSEMBLY

The optics depicted in FIG. 3 are shown in place in the pictorial illustration of FIG. 4. The laser gel scanner has been designed specifically to digitize the two-dimensional optical density information in 2-D gels. However, it will digitize any substantially transparent object, possibly containing absorbing or light scattering regions, provided that the object dimensionally fits on a gel stage 30. Wet and dry gels as well as autoradiograms may be scanned. The maximum gel size is 200×240 mm.

Refering to FIG. 4, the gel stage 30 is a rectangular-shaped frame that is designed to accomodate a glass gel holder, typically 200×240×9 mm., and transport it in the gel plane through the scan zone. When the unit scans wet gels, a glass gel holder with a raised lip (not shown) around the edge is typically used to confine the liquid. A glass cover plate (not shown) is also often used to flatten the gel surface. The gel stage 30 is designed to be introduced into the scanner assembly 39 which includes a base plate 41 and a pair of end plates 43 supported by rods 45. The various components of the optical system are located at various points on this assembly to form the folded beam, compact scanning system.

The scan zone is defined as that region in the gel plane that lies between the long-line photo sensor 28 and fourth folding mirror 22. The gel stage 30 comprises two apertured aluminum support plates 34, 36 that are connected by aluminum support tubes 38, 40. The stage 30 is mounted to slide along two steel support rods 42, 44 which define the gel plane so that the stage can be drawn through the scan zone by a continuous pulley 47, mounted pull string 46, the ends of which are secured to the stage at opposing attachment points 48. Pull string 46 is typically a high tensile-strength stainless-steel cable to minimize effects of both thermal and mechanical stresses on its elongation. Stage-position detectors 50 comprise pairs of LEDs and photosensors to signal when the stage is in either the "begin-scan", or "end of scan" positions.

Stage motor 32, typically a 1 RPM instrument gear motor with a constant speed and reversible field, is attached to the exterior surface of one of the two end plates 43 for the scanner assembly and turns drive capstan 52 which is keyed to the motor shaft. Pull string 46 is tightly wrapped around capstan 52, at least four times, for positive traction so that as the capstan turns, the stage translates smoothly through the scan zone in the signalled direction, at a constant speed. Simultaneously, it is transversely scanned by the scanning beam which passes through the gel to the diode sensor 28.

GEL SCANNER ELECTRONICS AND DATA INTERFACE SYSTEM

Figure 5A:
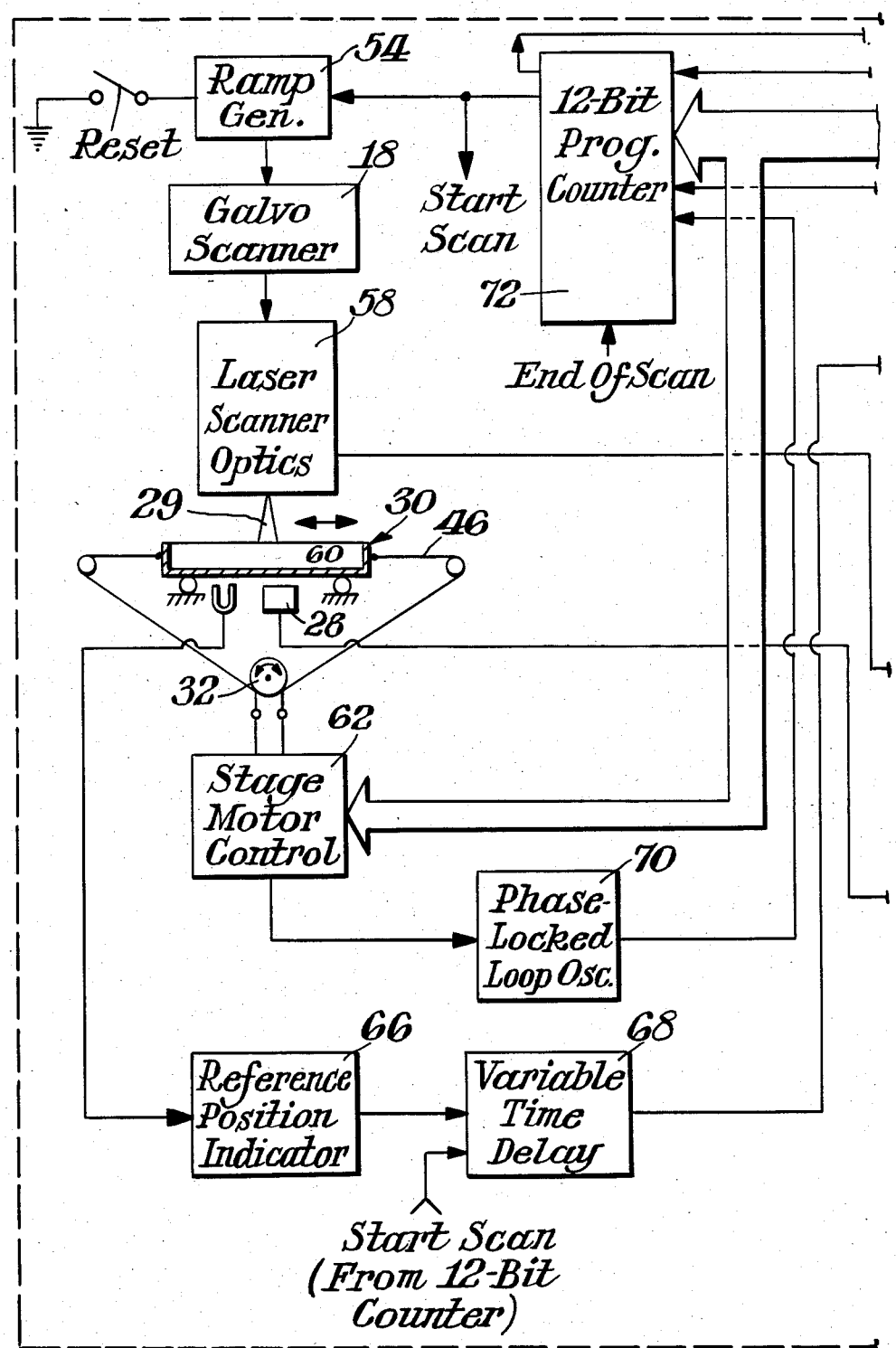
FIGS. 5A and 5B are block diagrams of the scanner electronics and data interface system used in this invention.
Figure 5B:
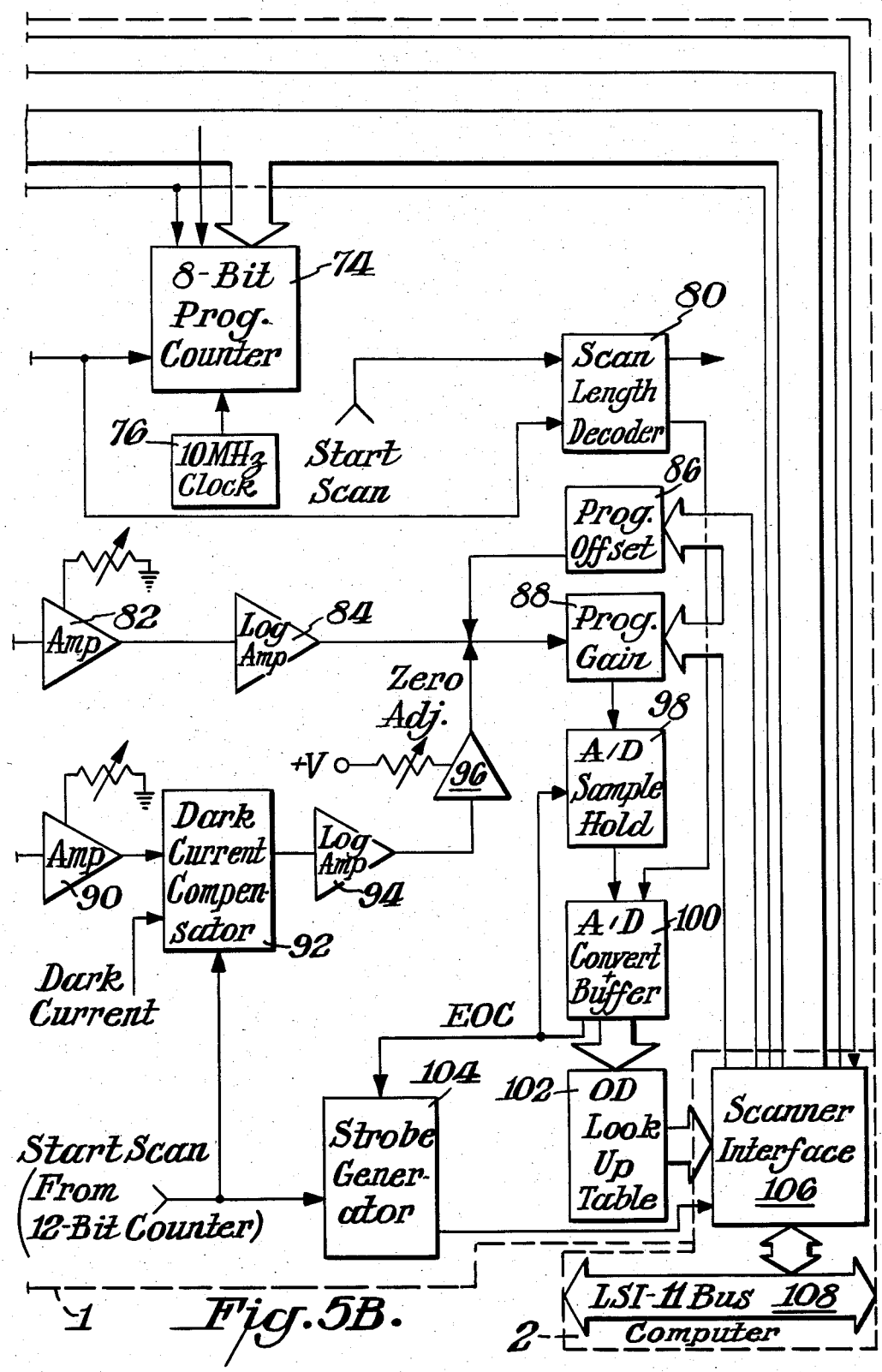

Depicted in FIGS. 5A and 5B are block diagrams of the gel scanner and data interface system. The laser gel scanner system 1 interfaces the computer 2 via a scanner interface 106 which in turn interfaces an LSI-11 Bus 108. All communication to the scanner system is conducted through the scanner interface 106. Thus, the computer controls the stage motor control 62, a 12-Bit programmable counter 72, an 8-Bit programmable counter 74, a programmable gain circuit 88, and a programmable offset circuit 86. These functions are all interrelated such that the laser scanner precisely scans the gel in a fashion that enables the two-dimensional optical density information to be digitized for use during analysis by the software.

In order to provide precise synchronization between the stage position and the initiation of each scan, zero-crossings of the stage motor 32 supply voltage waveform are used to toggle a 6 kHz phase-locked loop oscillator 70 which, in turn, clocks a row-spacing 12-Bit programmable counter 72. The synchronized periodic start-scan signals produced by the 12-Bit counter 72 are spaced according to instructions programmed by the operator via the scanner interface 106 to establish row spacing, and the separation between successive scan lines.

More specifically, the start scan signal does the following:

1. It causes the galvanometer ramp generator 54, to produce a saw-tooth waveform needed to deflect the galvanometer scanner mirror 16 (FIGS. 3 and 4) and sweep the laser beam across a gel 60 in the gel stage 30. The ramp generator 54 is provided with a manual reset switch that may be used to stop the scan without affecting the stage movement.
2. It enables the variable time delay circuit 68 such that is is ready to respond to the reference-position indication signal from the reference-position indicator 66, which is coupled to the reference-position photodetector 50. The variable time-delay circuit 68 provides the means by which the operator can manually select a prescribed portion of the gel (in terms of pixels in the scan direction, or columns) to be scanned.
3. When combined with the output of the column-spacing 8-Bit programmable counter 74 it provides the enabling signal for the scan-length decoder 80. The 8-Bit column counter 74 performs a similar function as the 12-Bit programmable counter 72 in that it receives pixel-spacing information from the operator via the scanner interface 106 and signals the occurrence of the end of each scan to the scan length decoder 80. The scan-length decoder 80 generates (a) an end of scan signal and transmits it to the 12-Bit programmable counter 72, which in turn, transmits a clear address signal to the scanner interface 106, and (b) a convert signal to the A/D converter 100. A 10 MHz clock 76 is used to increment the 8-Bit column-spacing counter 74. The scanner interface 106 transmits scan enable and counter load signals to the respective counters.
4. The start-scan signal also activates the dark current compensator 92 for measuring a representative photodetector dark current/voltage from the gel-free portion of the scan for subtraction from the instantaneous analytical signal for calibration purposes.
5. Finally, the start-scan signal enables each EOC (End of Convert) status ssignal to strobe 104 the A/D converted data via the A/D converter 100 in the buffer registers 100 into the scanner interface 106.

The last circuit to be described is the OD (Optical Density) analyzer. The principal inputs to this circuit are the reference signal and the analytical signal which are obtained from the action of the galvo deflector 18 passing the scanning laser beam through the laser scanner optics 58 through the gel 60 onto the long-line photodector 28. In addition, programmable gain 88 and programmable offset 86 parameters are input to this circuit from the computer via the scanner interface 106. These parameters are used to optimize the digitization of pixel OD values.

In operation the reference and analytical signals are separately amplified logarithmically via the operational amplifier 82, 84 in the reference line and 90, 94 in the analytical line. These signals are then summed with the programmed offset value at a summing junction where the log (A/R) result is formed. Manual controls are provided for the operator to make zero-adjust corrections 96 to the analytical signal prior to its appearance at the summing junction. The settings are made based on OD values existing at the outset of each scan in the calibration series.

The programmable-gain circuit 88 is configured to enable the operator to manually select either high or low OD ranges and make full-scale adjustments for them upon prompting by the computer should the operator know ahead of time what high and low OD limits are needed for the gel to be scanned. This feature is provided in addition to its normal function of automatically applying gain values to the ratio signals present at the summing junction using values transmitted to it from the scanner interface 106.

The A/D sample/hold circuit 98 samples the scan signals at a programmed rate, and transmits the held voltages directly to the A/D converter 100 for processing into 8-Bit format. The output data terminals of the A/D converter are connected to a set of buffer registers for storing each scan's data in 12-Bit format. The buffer register output terminals are in turn connected to a lookup table memory 102, which communicates the digitized OD values to the scanner interface 106, the OD values are represented by eight data bits.

The A/D converter 100 responds to a convert signal that is generated by the scan-length decoder 80 at the end of each scan. Upon its receipt, the A/D converter 100 loads the buffer registers and generates end of converter (EOC) signal pulses to the A/D sample/hold 98 and strobe-generator circuits 104 to simultaneously load new data into the A/D converter 100 while the preceeding scan's data is entered onto the computer via the scanner interface 106.

During the operation of the scanner, a reference position indicator 66 is positioned at one of the scan extremes to sense the beginning of each scan needed to initiate the operation of the scanner/stage motor controller 62. A split photodector 50 has been found useful for this purpose by generating a sharply rising trigger pulse that contributes substantially to the precision of scan direction displacement (column) measurements.

III: COMPUTER SYSTEM

The last module which will be discussed in detail is the computer system 2 and 3 (FIG. 1) used with the gel scanner. Illustrated in FIG. 6 is a detailed block diagram of the computer 2, the interface modules 106, 114, 116, 118, 120 its peripherals and memory module 110, 112. The system's peripherals includes blocks 124, 126, 128, 130, the analysis software 4 and the computer memory modules 110, 112. The LSI-11 Bus 108 serves as the main communication link to all the major system components.

The computer serves many functions, several of which are specific to 2-D gel analysis. It transmits the scan parameters to the scanner interface 106 which in turn passes these parameters to the gel scanner 1. It both receives and transmits data from the various peripheral interfaces 114, 116, 118, 120 to the associated system peripherals 124, 126, 128, 130 which are directly accessible by the operator. It processes the 2-D data using the analysis software 4 that resides in the main Random-Access Memory 110 and interacts with the image memory 112 during system operation. In addition, the computer controls the movement of data to and from the major components of the system via the LSI-11 data Bus 108. Each of these major components will be described in more detail below.

The computer 2, is a DEC (Digital Equipment Corporation) LSI-11/23 microcomputer with 256K bytes of main memory. The operating system is DEC's single-user system, RT-11 version 4. The computer uses the Random-Access Memory 110 to store both programs and data. As mentioned above the LSI-11 Bus 108 serves as the main communication link to all the major system components.

The image-memory system 112 has been designed to store over four million 8-Bit samples per circuit board with integrated-circuit memories now readily available. The amount of data generated by the laser scanner system 1 is relatively large, at present typically over one million samples. These data must be stored in a place where access to them is random and rapid. The image memory 112 provides this function as follows. The image memory 112 which, consists of commercially available components, utilizes a 2048 word-wide address-window of the DEC LSI-11/23 computer 2 located in the I/O portion of the memory physical address space as the location where the scanned image data are accessed. This section of the I/O memory addresses is used to access a single horizontal line of pixels, all of which are contained in the image memory 112. The horizontal line appearing in the 2048 word window is specified by a number in a single register in a neighboring area of the I/O address region. Different lines may be made to appear in the 2048 word window by changing the horizontal line pointer in this register.

The system peripherals 3 are detailed in FIG. 6 as items 124, 126, 128 and 130. An interface module 114, 116, 118, and 120 is associated with each peripheral as a means for providing the correct communications link between the computer Bus 108 and the operator. The CRT terminal 124 is a conventional terminal used by the operator to control the operation of the laser gel scanner instrument. The interface associated with the terminal is an RS-232 serial interface 114 which is linked directly to the LSI-11 Bus 108. The RGB monitor 126 is a color display monitor that accepts an RS-170 video signal from the display memory and control interface 116 via the LSI-11 Bus 108. The display memory and control interface 116 stores a portion of the gel image which is continuously displayed on the RGB monitor 126. The display memory array is arranged as 480 rows with 512 picture elements (pixels) per row. Both the RGB monitor 126 and the display memory and control interface are commercially available. The printer 128 and its serial interface 118 both of which are commercially available, are used to generate hard copy information generated as a result of the gel analysis. A Winchester DSD 880 Floppy Disk drive 130, a disk interface 120 and the Winchester 30 megabyte disk 122 in combination provide the system with an adequate amount of data mass-storage capability.

The method and apparatus of this invention are thus seen to provide a rapid, efficient means of resolving and quantitating image spot information from whatever source derived.

APPENDIX 1

```
C
C
C     PROGRAM NAME: SURF6.FOR
C
C        ****** 2D GEL ANALYSIS SOFTWARE ******
C
C            ****** MAINLINE ROUTINE ******
C
C     THIS IS THE EPL IMAGE MEMORY VERSION OF SURF. IN THIS VERSION THE
C     DATA ARE STORE IN THE 1024 X 1024 BYTE EPL MEMORY SYSTEM.
C
C     THIS VERSION OF SURF OPERATES UNDER RT-11 V4 ON THE
C     PDP 11/23.
C
C     THIS VERSION OF SURF USES THE NEW ALGORITHM TO ANALYZE THE TWO
C     DIMENSIONAL OPTICAL DENSITY PROFILE OF 2D ELECTROPHORETIC GELS.
C
C
C     THE NEW ALGORITHM IS DESCRIBED BRIEFLY BELOW.
C
C     THE SURFACE TO BE ANALYZED CONSISTS OF A TWO DIMENSIONAL DISTRIBUTION
C     OF OPTICAL DENSITY, IN WHICH THERE EXISTS MANY REGIONS OF HIGH
C     DENSITY THAT WE SHALL HEREAFTER CALL SPOTS. IN GENERAL, THESE SPOTS
C     ARE SOMEWHAT GAUSSIAN SHAPED AND THEREFORE THE MATHEMATICAL MODEL
C     THAT IS USED TO QUANTITATE THE SURFACE IS A TWO DIMENSIONAL GAUSSIAN.
C
C     IN THIS VERSION OF SURF, SURF6.FOR, THE ENTIRE SURFACE IS ANALYZED
C     IN ONE PROGRAM PASS RATHER THAN SEVERAL PASSES.
C     MOST OF THE ARITHEMETIC
C     OPERATIONS ARE INTEGER WHICH ENHANCES THE COMPUTATION SPEED.
C
C     THE PROGRAM STEPS ARE AS FOLLOWS:
C
C     IT IS ASSUMED THAT THE GEL IMAGE DATA ARE ALREADY IN THE
C     EPL IMAGE MEMORY.
C
C     1. FIND THE MAXIMUM PIXEL VALUE FOR EACH LINE IN THE N x M ANALYSIS
C        REGION THAT WAS SPECIFIED BY THE COORDINATES ISTART, ISTOP, JSTART,
C        AND JSTOP AND STORE THESE IN A ZMAX TABLE.
C
C     2. LOCATE THE MAXIMUM PIXEL AMONG THE M LINES
C
C     3. STARTING AT THE MAXIMUM PIXEL FIND FOUR ORTHOGONAL INFLECTION
C        POINTS USING A 15 SAMPLE SAVITZKY AND GOLAY POLYNOMIAL.
C
C     4. SUBTRACT A TWO DIMENSIONAL GAUSSIAN FROM THE SURFACE USING THE
C        MAXIMUM PIXEL VALUE AND THE FOUR INFLECTION POINTS AS PARAMETERS
C        TO CONSTRUCT THE FUNCTION.
C
C     5. UPDATE THE MAX TABLE, I.E. FIND THE NEW MAXIMUM PIXEL VALUE
C        IN EACH LINE THAT HAD BEEN ACCESSED DURING THE SUBTRACTION ROUTINE.
C
C     6. REPEAT THE SEQUENCE STARTING WITH #2 UNTIL THE REMAINING MAXIMUM
C        PIXEL IS BELOW THE THRESHOLD.
C
C
C     CODE BY:  J. G. ELIAS
C               ENGINEERING PHYSICS LABORATORY
C               DUPONT EXPERIMENTAL STATION
C               WILMINGTON, DELAWARE 19898.
C
C
C     COORDINATE SYSTEM CONVENTIONS
C
C     * ALL COORDINATES ARE RELATIVE TO THE FACE OF THE VIDEO DISPLAY.
C
C     * THE ORIGIN, (0,0), IS IN THE LOWER LEFT HAND CORNER
C
C     * THE LETTER I REPRESENTS HORIZONTAL POSITIONS
C
C     * THE LETTER J REPRESENTS VERTICAL POSITIONS
```

```
C      PROGRAM VARIABLE DEFINITIONS
C
C      ISTART   : THIS IS THE LEFT HAND VERTICAL ANALYSIS BOUNDARY.
C                 DATA TO THE LEFT OF THIS IS IGNORED.
C
C      ISTOP    : THIS IS THE RIGHT HAND VERTICAL ANALYSIS BOUNDARY.
C                 DATA TO THE RIGHT OF THIS IS IGNORED.
C
C      JSTART   : THIS IS THE BOTTOM HORIZONTAL ANALYSIS BOUNDARY.
C                 DATA BELOW THIS IS IGNORED.
C
C      JSTOP    : THIS IS THE TOP HORIZONTAL ANALYSIS BOUNDARY.
C                 DATA ABOVE THIS IS IGNORED.
C
C      IZM(N)   : THIS ARRAY CONTAINS THE VALUE OF THE MAXIMUM
C                 PIXEL FOR EACH LINE OF SURFACE DATA
C                 IT IS THIS ARRAY THAT IS SEARCHED EVERY TIME
C                 A NEW MAXIMUM IS NEEDED.
C
C      MIM(N)   : THIS ARRAY CONTAINS THE COLUMN LOCATION OF THE
C                 MAXIMUM IN EACH OF THE IZM() LOCATIONS.
C
C      ISIG1    : ISIG1 IS PROPORTIONAL TO THE LEFT HAND INFLECTION POINT
C                 IN THE I DIRECTION.
C
C      ISIG2    : ISIG2 IS PROPORTIONAL TO THE RIGHT HAND INFLECTION POINT
C                 IN THE I DIRECTION.
C
C      JSIG1    : JSIG1 IS PROPORTIONAL TO THE BOTTOM INFLECTION POINT IN
C                 THE J DIRECTION.
C
C      JSIG2    : JSIG2 IS PROPORTIONAL TO THE TOP INFLECTION POINT IN
C                 THE J DIRECTION.
C
C      I0       : THIS IS THE I LOCATION OF THE PIXEL MAXIMUM.
C
C      J0       : THIS IS THE J LOCATION OF THE PIXEL MAXIMUM.
C
C      IA0      : THIS IS THE VALUE OF THE PIXEL MAXIMUM.
C
C      I1       : THIS IS THE VERTICAL SUBTRACTION BOUNDARY TO THE
C                 LEFT OF I0
C
C      I2       : THIS IS THE VERTICAL SUBTRACTION BOUNDARY TO THE
C                 RIGHT OF I0
C
C      J1       : THIS IS THE HORIZONTAL SUBTRACTION BOUNDARY BELOW J0
C
C      J2       : THIS IS THE HORIZONTAL SUBTRACTION BOUNDARY ABOVE J0
C
C      IPOINT   : IPOINT INDICATES THE TOTAL NUMB' OF GAUSSIANS
C                 THAT HAVE BEEN ESTIMATED AND SUBTRACTED.
C
C      ICUTOF   : THIS IS THE PIXEL CUTOFF VALUE. WHEN THE LARGEST
C                 PIXEL REMAINING ON THE SURFACE IS LESS THAN
C                 ICUTOF THEN THE SURFACE ANALYSIS IS HALTED.
C
C      IPRVOL   : REDUCED VOLUME IN THE POSITIVE I DIRECTION
C      RVOLIP   : FLOATING POINT EQUIVALENT OF IPRVOL
C
C      IMRVOL   : REDUCED VOLUME IN THE NEGATIVE I DIRECTION
C      RVOLIM   : FLOATING POINT EQUIVALENT OF IMRVOL
C
C      JPRVOL   : REDUCED VOLUME IN THE POSITIVE J DIRECTION
C      RVOLJP   : FLOATING POINT EQUIVALENT OF JPRVOL
C
C      JMRVOL   : REDUCED VOLUME IN THE NEGATIVE J DIRECTION
C      RVOLJM   : FLOATING POINT EQUIVALENT OF JMRVOL
C
C      TVOL     : TOTAL REDUCED VOLUME ACCUMULATOR
C
```

```
C FOR RT-11 SYSTEMS LINK THIS PROGRAM WITH
C
C       1.  S5.MAC:     ASYMMETRIC GAUSSIAN SUBTRACTION ROUTINE
C
C       2.  IN5.FOR:    15 SAMPLE POLYNOMIAL INFLECTION POINT
C                       FINDER.
C
C       3.  ISUM.MAC:   USED WITH IN5 TO SUM OVER SEVEN ROWS OR COLUMNS
C
C       4.  Z5.MAC:     MAXIMUM PIXEL SEARCHING ROUTINE
C
C       5.  CORI.FOR:   PARAMETER INPUT ROUTINE
C
C
        COMMON /BLK1/ISTART,ISTOP,JSTART,JSTOP
        COMMON /BLK2/IZM(1024),MIM(1024)
        COMMON /BLK3/IZLOG(2800),IJTAB(4000)
        COMMON /BLK4/IPRVOL(2),IMRVOL(2),JPRVOL(2),JMRVOL(2),IGVOL(2)
        COMMON /BLK5/ISIG1,ISIG2,JSIG1,JSIG2,I0,J0,IA0
C
C
        LOGICAL*1 IANS,INAM(15)
C
C
        MERR=0
        TVOL=0
C
C GET ANALYSIS BOUNDARIES
C
        CALL CORI
C
        WRITE(5,1000)
1000    FORMAT('$ENTER CUTOFF PIXEL INTENSITY(0-255)(I6): ')
        READ(5,2000)ICUTOF
2000    FORMAT(I6)
C
C READ IN THE MAXIMUM NUMBER OF GAUSSIANS THAT ARE ALLOWED
C BEFORE PROGRAM EXECUTION IS SUSPENDED
C
2050    WRITE(5,2100)
2100    FORMAT('$ENTER MAXIMUM GAUSSIAN NUMBER( <1000)(I6): ')
2200    READ(5,2000)NGAUSS
C
        IF(NGAUSS .GT. 1000 .OR. NGAUSS .LE. 0)GOTO 2050
C
        IPOINT=0
C
C
C CALCULATE THE GAUSSIAN DATA TABLE THAT
C IS USED IN SUBROUTINE S5
C
C
C
        M=500
C
C LOAD THE IZLOG TRANSFORMATION TABLE.
C
        DO 3000 J=1,255
C
            Z=J
            I1=INT(M*ALOG(Z))+1
            I2=INT(M*ALOG(Z+1))+1
C
            DO 2500 K=I1,I2
C
                IZLOG(K)=J
2500            CONTINUE
3000    CONTINUE
C
C LOAD THE IJTAB LOOKUP TABLE.
C
```

```
          YC=5.00125E-04
C
          DO 4000 K=1,4000
C
             SIG=YC*(K-1)
             IJTAB(K)=INT(M*SIG*SIG)
4000         CONTINUE
C
C FILL ZMAX TABLES, IZM() AND MIM().
C ZMAXAL LOCATES THE MAXIMUM PIXEL IN EACH LINE OF THE
C SELECTED ANALYSIS REGION
C
          CALL ZMAXAL
C
C
C FIND MAXIMUM PIXEL IN IZM TABLE
C
5000      CALL ZMAX
C
C
C
C CHECK TO MAKE SURE THE MAXIMUM PEAK IS ABOVE
C CUTOFF. IF IT IS NOT THEN BRANCH TO 12000 TO END ANALYSIS.
C
          IF(IA0.LT.ICUTOF.OR.IPOINT.GT.NGAUSS)GOTO 12000 !QUIT
C
C
C SEARCH FOR INFLECTION POINTS
C
          CALL INFLEC
C
C
C CALCULATE THE EXTENT OF THE SUBTRACTION AREA. THIS AREA MUST NOT
C EXCEED A CERTAIN MAXIMUM VALUE WHICH DEPENDS ON THE PIXEL AMPLITUDE.
C OTHERWISE NEGATIVE ADDRESSES WILL BE GENERATED IN THE LOGARITHMIC
C LOOKUP TABLE, I.E.
C
C    ALOG(A0) MUST BE GREATER THAN ((I-I0)/ISIG)**2) + ((J-J0)/JSIG)**2
C
C TO SOLVE THIS EQUATION WE ASSUME THAT (I-I0)/(J-J0) = ISIG/JSIG
C THEREFORE,
C
C         (J-J0) = SQRT{ (1/2)*LOG(A0) }*JSIG
C AND
C
C         (I-I0) = SQRT{ (1/2)*LOG(A0) }*ISIG
C
          A0=IA0
          X=SQRT(.5*ALOG(A0))
C
C CALCULATE SUBTRACTION LIMITS
C
          I1=MAX0(I0-INT(X*ISIG1+1),ISTART-3)    !LEFT HAND LIMIT
          I2=MIN0(I0+INT(X*ISIG2-1),ISTOP+3)     !RIGHT HAND LIMIT
          J1=MAX0(J0-INT(X*JSIG1+1),JSTART-3)    !BOTTOM LIMIT
          J2=MIN0(J0+INT(X*JSIG2-1),JSTOP+3)     !TOP LIMT
C
C
C SUBTRACT THE GAUSSIAN ESTIMATE FROM THE GEL IMAGE SURFACE
C
          IAC=INT(M*ALOG(A0))
          CALL SUBTR(IAC,I1,I2,J1,J2)
C
C CONVERT THE 32 BIT REDUCED VOLUME DATA TO FLOATING POINT
C
          JJ=IAJFLT(IPRVOL,RVOLIP)
          JJ=IAJFLT(IMRVOL,RVOLIM)
          JJ=IAJFLT(JPRVOL,RVOLJP)
          JJ=IAJFLT(JMRVOL,RVOLJM)
          JJ=IAJFLT(IGVOL,GVOL)
C
```

```
C CALCULATE THE GAUSSIAN VOLUME, XCONST
C
        PI=3.1416
        XCONST=PI*0.25*((ISIG1+ISIG2)*(JSIG1+JSIG2))
C
C CALCULATE THE REDUCED VOLUME, RV0
C
        RV0=GVOL-(RVOLJM + RVOLJP)
C
C ACCUMULATE TOTAL REDUCED VOLUME
C
        TVOL = TVOL + RV0

C
C CALCULATE CENTERS OF MASS
C
C       J DIRECTION CENTER OF MASS, CMJ
C
        SRPI=SQRT(PI)
C
        VJP=(PI/8.)*IA0*JSIG2*(ISIG1+ISIG2)
        VJM=(PI/8.)*IA0*JSIG1*(ISIG1+ISIG2)
        CMJ=((VJP-RVOLJP)*(JSIG2/SRPI)-(VJM-RVOLJM)*(JSIG1/SRPI))/RV0 + J0
        JCM=CMJ
C
C       I DIRECTION CENTER OF MASS, CMI
C
        VIP=(PI/8.)*IA0*ISIG2*(JSIG1+JSIG2)
        VIM=(PI/8.)*IA0*ISIG1*(JSIG1+JSIG2)
        CMI=((VIP-RVOLIP)*(ISIG2/SRPI)-(VIM-RVOLIM)*(ISIG1/SRPI))/RV0 + I0
        ICM=CMI
C
C
C CALCULATE THE REDUCED AMPLITUDE FROM THE GAUSSIAN
C VOLUME AND THE REDUCED VOLUME.
C
        IF(INT(RV0/XCONST) .GT. IA0)WRITE(5,6500)
 6500   FORMAT(' REDUCED AMP GT PEAK AMP')
        IA0=INT(RV0/XCONST)
C
C
C OUTPUT THE GAUSSIAN PARAMETERS TO FILE FTN2.DAT
C
        WRITE(2,10000)IA0,I0,J0,ISIG1,ISIG2,JSIG1,JSIG2,ICM,JCM
10000   FORMAT(1X,9I5)
C
        WRITE(5,10100)IPOINT,IA0,I0,J0,ISIG1,ISIG2,JSIG1,JSIG2
10100   FORMAT(8(2X,I6))
C
C INCREMENT THE GAUSSIAN COUNTER
C
        IPOINT=IPOINT+1
C
C
C GO BACK TO BEGINNING OF LOOP
C
        GOTO 5000
C
C END OF ANALYSIS
C
12000   CONTINUE
C
        WRITE(5,13000)TVOL,IPOINT
13000   FORMAT(' TOTAL RELATIVE VOLUME = ',E10.4,/,
     &         ' ACCOUNTED BY ',I6,' GAUSSIANS')
C
        CLOSE(UNIT=2)
C
        STOP
        END
```

```
; PROGRAM NAME: Z5.MAC
;
;       ***** 2D GEL ANALYSIS SOFTWARE ******
;
;       ***** MAXIMUM PIXEL SEARCHING ROUTINE *****
;
; ROUTINE ZMAXAL FINDS THE MAXIMUM PIXEL IN EACH LINE OF A N
; COLUMN BY M LINE PIXEL AREA OF THE EPL IMAGE MEMORY. THE
; MAXIMUM VALUE FOR EACH LINE AND ITS HORIZONTAL POSITION ARE STORED
; IN TWO 1024 WORD ARRAYS: IZM() CONTAINS THE MAXIMUM PIXEL AMPLITUDE
; FOR EACH LINE AND MIM() HOLDS ITS HORIZONTAL POSITION. THE SIZE OF
; THE SEARCH AREA IS DETERMINED BY FOUR NUMBERS, RELATIVE TO
; THE FACE OF THE VIDEO MONITOR:
;
;       1. ISTART= THE LEFT HAND VERTICAL BOUNDARY
;       2. ISTOP = THE RIGHT HAND VERTICAL BOUNDARY
;       3. JSTART= THE BOTTOM HORIZONTAL BOUNDARY
;       4. JSTOP = THE TOP HORIZONTAL BOUNDARY
;
; THE PIXEL COORDINATES ARE DENOTED BY VARIABLES I AND J.
; WHERE I IS THE HORIZONTAL POSITION(0-1023) AND J IS THE
; VERTICAL POSITION(0-1023) RELATIVE TO THE VIDEO MONITOR.
; I=0, J=0 IS THE LOWER LEFT HAND CORNER OF THE SCREEN.
;
; ROUTINE ZMAX SEARCHES ARRAY IZM() AND LOCATES THE MAXIMUM
; PIXEL VALUE. THE PIXEL VALUE, IA0, ITS HORIZONTAL POSITION, I0,
; AND ITS VERTICAL POSITION, J0, ARE RETURNED TO THE CALLING
; PROGRAM.
;
; ROUTINE ZMAXUP SEARCHES ONE LINE OF IMAGE DATA AND LOCATES
; THE MAXIMUM PIXEL IN THAT LINE. AFTER FINDING THE MAXIMUM PIXEL
; ITS AMPLITUDE AND HORIZONTAL POSITION ARE STORED IN IZM() AND
; MIM() RESPECTIVELY. THIS ROUTINE IS CALLED EVERY TIME PIXEL
; VALUES ARE ALTERED WITHIN A LINE OF IMAGE DATA.
;
; CODE BY J.G. ELIAS , EPL DUPONT EXPERIMENTAL STATION
; WILMINGTON, DE.                      DEC-20-81
;
;
; COMMON BLOCK, BLK1, CONTAINS THE BOUNDARIES FOR THE DATA
; ANALYSIS. SEE PROGRAM 'SURF6.FOR' FOR MORE DETAILS.
;
        .PSECT  BLK1    GBL,D,OVR,RW,REL
ISTART: .BLKW   1
ISTOP:  .BLKW   1
JSTART: .BLKW   1
JSTOP:  .BLKW   1
;
;
; COMMON BLOCK, BLK2, CONTAINS THE ZMAX TABLES. SEE PROGRAM
; 'SURF6.FOR' FOR MORE DETAILS.
;
        .PSECT  BLK2    GBL,D,OVR,RW,REL
IZM:    .BLKW   2000
MIM:    .BLKW   2000
;
;
        .PSECT  Z5
        .GLOBL  ZMAXAL,ZMAX,ZMAXUP,YADDR,XADDR
        ;
IM:     .WORD   0               ; START OF TEMPORARY
JMAX:   .WORD   -20000          ; VARIABLES
IMAX:   .WORD   0               ;
ATEM:   .WORD   0               ;
BTEM:   .WORD   0               ;
CTEM:   .WORD   0               ;
PIX:    .WORD   0               ;
ROW:    .WORD   0               ;
                                ; END OF TEMP VARIABLES
```

```
;
;
; THIS PART OF Z5 SETS UP THE BOUNDARIES FOR ZMAXING THE
; N x M ANALYSIS REGION.
;
ZMAXAL: MOV    JSTOP,R0            ;SETUP FOR ROW LOOP
        SUB    JSTART,R0           ;COUNTER CALCULATION
        INC    R0
        MOV    ISTOP,IDIM          ;SETUP FOR COLUMN LOOP
        SUB    ISTART,IDIM         ;COUNTER CALCULATION
        INC    IDIM                ;INC FOR CORRECT COUNT
        MOV    JSTART,ROW          ;LOAD 1ST STARTING ROW
        DEC    ROW
        MOV    JSTART,ATEM
        ASL    ATEM                ;MUTIPLY BY TWO FOR ADDRESSING
        MOV    #IZM,R3             ;ZMAX TABLE POINTER
        ADD    ATEM,R3             ;ADD STARTING OFFSET
        MOV    #MIM,R4             ;IMAX TABLE POINTER
        ADD    ATEM,R4             ;ADD STARTING OFFSET
;
; LOOK FOR THE MAXIMUM PIXEL IN EACH ROW J, STORE ITS VALUE IN IZM(J)
; AND ITS HORIZONTAL POSITION IN MIM(J).
;
; START J LOOP
;
1$:     INC    ROW                 ;ADVANCE TO NEXT ROW
        MOV    ROW,@#YADDR         ;YADDR IS WRITE ONLY
        MOV    IDIM,R1             ;LOAD COLUMN LOOP COUNTER
        MOV    ISTART,R2           ;ADD STARTING OFFSET
        ADD    #XADDR,R2           ;POINT TO IMAGE DATA
        CLR    JMAX                ;CLEAR JMAX FOR NEXT LOOP
        CLR    PIX
;
; START I LOOP
;
2$:     MOVB   (R2)+,PIX           ;INTERMEDIATE PIX MUST BE
                                   ;USED TO AVOID SIGN EXTENSION
                                   ;IN MOVB TO REG INSTR
        CMP    JMAX,PIX            ;IS JMAX > THIS PIXEL?
        BPL    3$                  ;BR IF IT IS
        MOV    PIX,JMAX            ;OTHERWISE STORE NEW JMAX
        MOV    R2,IMAX             ;AND ITS COLUMN LOCATION
3$:     SOB    R1,2$               ;CK FOR END OF LOOP
        MOV    JMAX,(R3)+          ;STORE TABLE VALUE FOR THIS ROW
        SUB    #XADDR+1,IMAX
        MOV    IMAX,(R4)+          ;SAME FOR COLUMN LOCATION
        SOB    R0,1$               ;CK FOR END OF ROUTINE
        RETURN
;
;
; THIS ROUTINE FINDS THE MAXIMUM PIXEL VALUE AMONG THE
; IZM TABLE ELEMENTS AND RETURNS ITS AMPLITUDE AND
; COORDINATES TO THE CALLING PROGRAM.
;
; VARIABLE DEFINITIONS
;
; IA0= THE AMPLITUDE OF THE MAXIMUM PIXEL IN THE TABLE
; I0 = THE I COORDINATE OF IA0
; J0 = THE J COORDINATE OF IA0
;
;
; COMMON BLOCK, BLK5, CONTAINS THE GAUSSIAN PARAMETERS
; WHICH ARE USED IN SUBTRACTING OUT A TWO DIMENSIONAL
; GAUSSIAN FUNCTION FROM THE DATA.
;
        .PSECT BLK5    GBL,D,OVR,RW,REL
        SIG:   .BLKW   4
        I0:    .BLKW   1
        J0:    .BLKW   1
        IA0:   .BLKW   1
;
```

```
        .PSECT Z5
;
ZMAX:   CLR     R2                      ;LOAD INITIAL VALUE
        MOV     JSTOP,R0                ;SET LOOP COUNT
        SUB     JSTART,R0
        INC     R0
        MOV     JSTART,R1               ;POINT R1 TO TABLE START
        ASL     R1                      ;MULT FOR WORD ADDRESSING
        ADD     #IZM,R1                 ;POINT R1 TO FIRST ELEMENT
        MOV     JSTART,R3               ;SETUP FOR J COUNTER
        DEC     R3                      ;STARTING POSITION
;
; START SEARCH
;
1$:     INC     R3                      ;INC J COUNTER
        CMP     (R1)+,R2                ;IS IZM() > IA0
        BMI     2$                      ; BR IF NOT
        MOV     -2(R1),R2               ;LOAD IZM UPDATE
        MOV     3776(R1),R4             ;LOAD MIM UPDATE
        MOV     R3,R5                   ;STORE ZMAX ROW LOCATION
2$:     SOB     R0,1$                   ;CK FOR END OF SEARCH
;
        MOV     R2,IA0                  ;STORE MAX PIXEL VALUE
        MOV     R4,I0                   ;STORE IT'S I COORDINATE
        MOV     R5,J0                   ;STORE IT'S J COORDINATE
        RETURN
;
;
; THIS ROUTINE UPDATES THE ZMAX TABLES ONE ROW AT
; A TIME. UPDATING SHOULD OCCUR WHENEVER DATA ARE
; CHANGED SUCH AS IN THE SUBTRACTION ROUTINE. UPDATING
; IS PERFORMED ON THE ROW WHOSE ROW NUMBER IS CURRENTLY
; IN THE EPL MEMORY ROW ADDRESS REGISTER, YADDR. THE
; CURRENT ROW NUMBER MUST BE IN R4 BEFORE CALLING THIS
; ROUTINE BECAUSE YADDR IS WRITE ONLY.
;
;
ZMAXUP: MOV     ISTOP,R3                ;SETUP FOR LOOP
        SUB     ISTART,R3               ;COUNT CALC.
        INC     R3
        MOV     ISTART,R2               ;POINT TO 1ST ADDRESS
        ADD     #XADDR,R2               ;POINT TO IMAGE DATA
        CLR     R0                      ;CLEAR COMPARE VALUE
        CLR     PIX
;
;START LOOKING FOR NEW ZMAX IN THIS ROW
;
1$:     MOVB    (R2)+,PIX               ;GET PIXEL VALUE
        CMP     R0,PIX                  ;LOOK FOR NEW ZMAX
        BPL     2$                      ;BR TO 2$ IF JMAX>PIXEL
        MOV     PIX,R0                  ;STORE NEW ZMAX
        MOV     R2,R1                   ;& ITS COLUMN LOCATION
2$:     SOB     R3,1$                   ;LOOP THRU COLUMNS
;
;
        SUB     #XADDR+1,R1             ;SUB MEMORY OFFSET ADDRESS
        ASL     R4                      ;R4 CONTAINS CURRENT ROW #
        MOV     #IZM,R3                 ;POINT TO ZMAX TABLE
        ADD     R4,R3                   ;ADD OFFSET
        ADD     #MIM,R4                 ;
        MOV     R0,@R3                  ;STORE NEW ZMAX FOR THIS ROW
        MOV     R1,@R4                  ;STORE NEW COLUMN VALUE
        RETURN
;

.END
;
```

```
C
C PROGRAM NAME: CORI.FOR
C
C THIS PROGRAM READS THE GEL COORDINATE INFORMATION
C FROM DISK FILE "GEL.COR" AND STORES THE DATA IN COMMON
C LOCATIONS BLK1 AND BLK5.
C
C THE VARIABLES ARE DEFINED IN PROGRAM SURF5.FOR
C
      SUBROUTINE CORI
      COMMON /BLK1/ISTART,ISTOP,JSTART,JSTOP
      COMMON /BLK5/ISIG1,ISIG2,JSIG1,JSIG2,I0,J0,IA0
      OPEN(UNIT=4,NAME='GEL.COR',TYPE='OLD')
      READ(4,2000)ISTART,ISTOP,JSTART,JSTOP,IBAR,JBAR
2000  FORMAT(6I6)
C
C IBAR AND JBAR ARE THE DEFAULT VALUES USED IN THE BACKGOUND
C SUBTRACTION PROGRAMS, SCROIT,BSUBV, AND BSUBH. THESE DEFAULT
C VALUES ARE PASSED TO THE OTHER PROGRAMS THROUGH ISIG1,ISIG2,
C JSIG1, AND JSIG2.
C
      ISIG1=IBAR
      ISIG2=IBAR
      JSIG1=JBAR
      JSIG2=JBAR
C
      CLOSE(UNIT=4)
      RETURN
      END
C PROGRAM NAME: IN5.FOR
C
C ****** 2D GEL ANALYSIS SOFTWARE ******
C
C     **** INFLECTION POINT LOCATION ROUTINE ****
C
C THIS ROUTINE USES THE SAVITZKY AND GOLAY METHOD OF
C POLYNOMIAL FITTING TO LOCATE INFLECTION POINTS IN
C THE IMAGE DATA. IF THE DATA ARE GAUSSIAN SHAPED, i.e.
C
C     Z(I,J)=IA0*EXP(-((I-I0)/ISIG)**2)*EXP(-((J-J0)/JSIG)**2)
C
C WHERE Z(I,J) IS THE VALUE OF THE DATA AT POINT (I,J), THEN
C THE INFLECTION POINT AS DETERMINED BY THIS ROUTINE IS RELATED
C TO ISIG AND JSIG ACCORDING TO
C
C     ISIG = SQRT(2)*(INFLECTION POINT) + 1
C
C ADDING ONE TO THE RIGHT HAND SIDE IN THE ABOVE EQUATION TENDS
C TO OVERESTIMATE THE ACTUAL SIGMA SLIGHTLY. THIS IS DESIRABLE
C WHEN USED WITH THE REDUCED VOLUME SUBTRACTION METHOD.
C
C THIS PARTICULAR ROUTINE EMPLOYS A 15 POINT SMOOTHING FUNCTION.
C
C CALLING PROTOCOL:
C
C     CALL INFLEC
C
C
C INPUTS TO THIS ROUTINE ARE VIA COMMON AREAS BLK1 AND BLK5
C WHICH ARE DEFINED IN THE MAINLINE PROGRAM SURF6.FOR.
C
C CODE BY J.G. ELIAS, EPL, DUPONT EXPERIMENTAL STATION
C WILMINGTON,DELAWARE              DEC-16-81
C
C
      SUBROUTINE INFLEC
C
      COMMON /BLK1/ISTART,ISTOP,JSTART,JSTOP
      COMMON /BLK5/ISIG1,ISIG2,JSIG1,JSIG2,I0,J0,IA0
C
C
C
```

```
C THIS SECTION DETERMINES ISIG1
C
C       CALCULATE BOTTOM HORIZONTAL LIMIT
C
        J1=MAX0(J0-3,JSTART)
C
C       GET THE INITIAL SUMS ABOUT J0
C
        ISM7=ISUM2(I0+7,J1)
        ISM6=ISUM2(I0+6,J1)
        ISM5=ISUM2(I0+5,J1)
        ISM4=ISUM2(I0+4,J1)
        ISM3=ISUM2(I0+3,J1)
        ISM2=ISUM2(I0+2,J1)
        ISM1=ISUM2(I0+1,J1)
        IS0=ISUM2(I0,J1)
        ISP1=ISUM2(I0-1,J1)
        ISP2=ISUM2(I0-2,J1)
        ISP3=ISUM2(I0-3,J1)
        ISP4=ISUM2(I0-4,J1)
        ISP5=ISUM2(I0-5,J1)
        ISP6=ISUM2(I0-6,J1)
C
        IB=0
        KSTOP=I0-ISTART
        KK=I0-6
C
C       LOOP UNTIL INFLECTION POINT IS FOUND
C
        DO 100 L=1,KSTOP
C
        KK=KK-1
        IB=IB+1
        ISP7=ISUM2(KK,J1)
        DIFF=91.*(ISM7+ISP7)+52.*(ISM6+ISP6)+19.*(ISM5+ISP5)
     *       -8.*(ISM4+ISP4)-29.*(ISM3+ISP3)-44.*(ISM2+ISP2)
     *       -53.*(ISM1+ISP1)-56.*IS0
C
C       TEST FOR SIGN CHANGE, JUMP OUT OF LOOP IF IT CHANGES
C
        IF(DIFF.GE.0)GOTO 120
C
C       REASSIGN SUM INDICES
C
        ISM7=ISM6
        ISM6=ISM5
        ISM5=ISM4
        ISM4=ISM3
        ISM3=ISM2
        ISM2=ISM1
        ISM1=IS0
        IS0=ISP1
        ISP1=ISP2
        ISP2=ISP3
        ISP3=ISP4
        ISP4=ISP5
        ISP5=ISP6
        ISP6=ISP7
100     CONTINUE
C
C IF LOOP IS COMPLETED THEN INFLECTION POINT WAS NOT FOUND
C BEFORE LEFT VERTICAL LIMIT WAS REACHED. ISIG1 IS THEN
C ASSIGNED THE VALUE OF THIS LIMIT.
C
        ISIG1=IB
        GOTO 130
C
120     ISIG1=IB
C
C
```

```
130       ISIG1=IFIX(ISIG1*1.414-1.)
          ISIG1=MAX0(ISIG1,3)
C
C THIS SECTION DETERMINES THE VALUE OF ISIG2
C
C         GET INITIAL SUMS ABOUT J0
C
          ISM7=ISUM2(I0-7,J1)
          ISM6=ISUM2(I0-6,J1)
          ISM5=ISUM2(I0-5,J1)
          ISM4=ISUM2(I0-4,J1)
          ISM3=ISUM2(I0-3,J1)
          ISM2=ISUM2(I0-2,J1)
          ISM1=ISUM2(I0-1,J1)
          IS0=ISUM2(I0,J1)
          ISP1=ISUM2(I0+1,J1)
          ISP2=ISUM2(I0+2,J1)
          ISP3=ISUM2(I0+3,J1)
          ISP4=ISUM2(I0+4,J1)
          ISP5=ISUM2(I0+5,J1)
          ISP6=ISUM2(I0+6,J1)
C
          KSTART=I0+7
          IB=0
C
C         LOOP UNTIL INFLECTION POINT IS FOUND
C
          DO 200 KK=KSTART,ISTOP
C
             IB=IB+1
             ISP7=ISUM2(KK,J1)
             DIFF=91.*(ISM7+ISP7)+52.*(ISM6+ISP6)+19.*(ISM5+ISP5)
     *         -8.*(ISM4+ISP4)-29.*(ISM3+ISP3)-44.*(ISM2+ISP2)
     *         -53.*(ISM1+ISP1)-56.*IS0
C
C         TEST FOR SIGN CHANGE, JUMP OUT IF IT DID
C
             IF(DIFF.GE.0)GOTO 220
C
C         REASSIGN SUM INDICES
C
             ISM7=ISM6
             ISM6=ISM5
             ISM5=ISM4
             ISM4=ISM3
             ISM3=ISM2
             ISM2=ISM1
             ISM1=IS0
             IS0=ISP1
             ISP1=ISP2
             ISP2=ISP3
             ISP3=ISP4
             ISP4=ISP5
             ISP5=ISP6
             ISP6=ISP7
C
200          CONTINUE
C
C IF LOOP IS COMPLETED THEN INFLECTION POINT WAS NOT
C FOUND BEFORE RIGHT VERTICAL LIMIT WAS REACHED. ISIG2
C IS THEN ASSIGNED THE VALUE OF THIS LIMIT
C
          ISIG2=IB
          GOTO 230
C
220       ISIG2=IB
C
C         THIS SECTION DETERMINES THE VALUE OF JSIG1
C
```

```
8       ISIG2=IFIX(ISIG2*1.414-1.)
        ISIG2=MAX0(ISIG2,3)
C
        I1=MAX0(I0-3,ISTART)
C
C       GET INITIAL SUMS ABOUT I0
C
        ISM7=ISUM1(I1,J0+7)
        ISM6=ISUM1(I1,J0+6)
        ISM5=ISUM1(I1,J0+5)
        ISM4=ISUM1(I1,J0+4)
        ISM3=ISUM1(I1,J0+3)
        ISM2=ISUM1(I1,J0+2)
        ISM1=ISUM1(I1,J0+1)
        IS0=ISUM1(I1,J0)
        ISP1=ISUM1(I1,J0-1)
        ISP2=ISUM1(I1,J0-2)
        ISP3=ISUM1(I1,J0-3)
        ISP4=ISUM1(I1,J0-4)
        ISP5=ISUM1(I1,J0-5)
        ISP6=ISUM1(I1,J0-6)
        JB=0
C
        JS1=J0-7
C
C       LOOP UNTIL INFLECTION POINT IS FOUND
C
        DO 300 JJ=JS1,JSTART,-1
C
            JB=JB+1
            ISP7=ISUM1(I1,JJ)
            DIFF=91.*(ISM7+ISP7)+52.*(ISM6+ISP6)+19.*(ISM5+ISP5)
     *      -8.*(ISM4+ISP4)-29.*(ISM3+ISP3)-44.*(ISM2+ISP2)
     *      -53.*(ISM1+ISP1)-56.*IS0
C
C       TEST FOR SIGN CHANGE, JUMP OUT IF IT DID
C
            IF(DIFF.GE.0)GOTO 320
C
C       REASSIGN SUM INDICES
C
            ISM7=ISM6
            ISM6=ISM5
            ISM5=ISM4
            ISM4=ISM3
            ISM3=ISM2
            ISM2=ISM1
            ISM1=IS0
            IS0=ISP1
            ISP1=ISP2
            ISP2=ISP3
            ISP3=ISP4
            ISP4=ISP5
            ISP5=ISP6
            ISP6=ISP7
300     CONTINUE
C
C IF LOOP COMPLETED THEN THE INFLECTION POINT WAS NOT
C FOUND BEFORE THE BOTTOM HORIZONTAL LIMIT WAS REACHED.
C JSIG1 IS THEN ASSIGNED A VALUE EQUAL TO THIS LIMIT.
C
        JSIG1=JB
        GOTO 330
320     JSIG1=JB
C
C THIS SECTION DETERMINES JSIG2
C
330     JSIG1=IFIX(JSIG1*1.414-1.)
        JSIG1=MAX0(JSIG1,3)
```

```
C
C      GET INITIAL SUMS ABOUT I0
C
       ISM7=ISUM1(I1,J0-7)
       ISM6=ISUM1(I1,J0-6)
       ISM5=ISUM1(I1,J0-5)
       ISM4=ISUM1(I1,J0-3)
       ISM3=ISUM1(I1,J0-4)
       ISM2=ISUM1(I1,J0-2)
       ISM1=ISUM1(I1,J0-1)
       IS0=ISUM1(I1,J0)
       ISP1=ISUM1(I1,J0+1)
       ISP2=ISUM1(I1,J0+2)
       ISP3=ISUM1(I1,J0+3)
       ISP4=ISUM1(I1,J0+4)
       ISP5=ISUM1(I1,J0+5)
       ISP6=ISUM1(I1,J0+6)
C
C
       JB=0
       JS1=J0+7
C
C      LOOP UNTIL INFLECTION POINT IS FOUND
C
       DO 400 JJ=JS1,JSTOP
C
       JB=JB+1
       ISP7=ISUM1(I1,JJ)
       DIFF=91.*(ISM7+ISP7)+52.*(ISM6+ISP6)+19.*(ISM5+ISP5)
     *  -8.*(ISM4+ISP4)-29.*(ISM3+ISP3)-44.*(ISM2+ISP2)
     *  -53.*(ISM1+ISP1)-56.*IS0
C
C      TEST FOR SIGN CHANGE, JUMP OUT IF IT DID
C
       IF(DIFF.GE.0)GOTO 420
C
C      REASSIGN SUM INDICES
C
       ISM7=ISM6
       ISM6=ISM5
       ISM5=ISM4
       ISM4=ISM3
       ISM3=ISM2
       ISM2=ISM1
       ISM1=IS0
       IS0=ISP1
       ISP1=ISP2
       ISP2=ISP3
       ISP3=ISP4
       ISP4=ISP5
       ISP5=ISP6
       ISP6=ISP7
400    CONTINUE
C
C      IF LOOP COMPLETED THEN THE INFLECTION POINT WAS NOT
C      FOUND BEFORE TOP HORIZONTAL LIMIT WAS REACHED. JSIG2
C      IS THEN ASSIGNED THE VALUE OF THIS LIMIT.
C
       JSIG2=JB
       GOTO 430
C
420    JSIG2=JB
C
430    CONTINUE
       JSIG2=IFIX(1.414*JSIG2-1.)
       JSIG2=MAX0(JSIG2,3)
C
       RETURN
       END
```

```
;
; PROGRAM NAME: ISUM.MAC
;
;     ****** 2D GEL ANALYSIS SOFTWARE *****
;
;        **** PIXEL SUMMING ROUTINE FOR INFLECTION POINT FINDING ****
;
; THIS PROGRAM IS USED WITH PROGRAM IN5.FOR TO LOCATE INFLECTION POINTS
; IN A TWO DIMENSIONAL DATA ARRAY. THE DATA ARE STORED IN THE EPL IMAGE
; PROCESSING MEMORY SYSTEM WHICH MUST BE CONFIGURED AS 1024 X 1024 BYTES
; FOR THIS PROGRAM IMPLEMENTATION.
;
; FUNCTION ISUM1 WILL SUM SEVEN ARRAY ELEMENTS ALONG ONE ROW.
;
; FUNCTION ISUM2 WILL SUM SEVEN ARRAY ELEMENTS ALONG ONE COLUMN.
;
; CALLING PROTOCOL
;
;        ISUM1=(I,J)      WHERE I IS THE STARTING COLUMN ELEMENT AND
;                         J IS THE ROW NUMBER IN WHICH THE SUM IS TAKEN.
;
;        ISUM2=(I,J)      WHERE J IS THE STARTING ROW ELEMENT AND I
;                         IS THE COLUMN NUMBER IN WHICH THE SUM IS TAKEN.
;
; THE EPL MEMORY SYSTEM MUST BE ENABLED BEFORE THE FIRST CALL TO THIS
; ROUTINE.
;
; CODE BY J.G. ELIAS, ENGINEERING PHYSICS LABORATORY, DUPONT
; EXPERIMENTAL STATION, WILMINGTON, DE., AUG-4-1982
;
;
;
PIX:    .WORD   0
;
        .GLOBL  ISUM1,ISUM2,YADDR,XADDR
;
ISUM1:  MOV     @2(R5),R2               ;GET STARTING COLUMN #
        ADD     #XADDR,R2               ;ADD OFFSET
        MOV     @4(R5),@#YADDR          ;LOAD ROW #
        CLR     R0
        MOV     #7,R1                   ;R1 IS THE COUNTER
        CLR     PIX
;
1$:     MOVB    (R2)+,PIX               ;NOTE: LOCATION PIX MUST BE
        ADD     PIX,R0                  ;USED TO AVOID SIGN EXTEND IN
                                        ;THE MOVB TO REG INSTR.
        SOB     R1,1$                   ;LOOP SEVEN TIMES
;
        RETURN
;
;
ISUM2:  MOV     @2(R5),R2               ;GET STARTING COLUMN #
        ADD     #XADDR,R2               ;ADD OFFSET
        MOV     @4(R5),R3               ;R3 IS ROW POINTER
        MOV     #7,R1                   ;R1 IS COUNTER
        CLR     PIX
        CLR     R0
        MOV     #YADDR,R4               ;R4 POINTS TO ROW REG
;
1$:     MOV     R3,@R4                  ;NOTE: R3 MUST BE USED AS
        INC     R3                      ;INTERMEDIATE BECAUSE YADDR
                                        ;IS WRITE ONLY
        MOVB    @R2,PIX                 ;NOTE: SEE PIX NOTE ABOVE
        ADD     PIX,R0                  ;ACCUMULATE SUM
        SOB     R1,1$                   ;LOOP SEVEN TIMES
;
        RETURN
;
        .END
```

```
; PROGRAM NAME: S5.MAC
;
;       ****** 2D GEL ANALYSIS SOFTWARE *******
;
;       ***** GAUSSIAN SUBTRACTION ROUTINE *****
;
; THIS ROUTINE SUBTRACTS A 2-D GAUSSIAN FUNCTION FROM THE IMAGE
; DATA CENTERED ABOUT I0 AND J0. THE DATA ARE STORED IN THE EPL
; IMAGE MEMORY SYSTEM WHICH SHOULD BE CONFIGURED AS 1024 X 1024
; BYTES FOR THIS PROGRAM IMPLEMENTATION. THE AMPLITUDE OF THE
; FUNCTION IS IA0, ITS HORIZONTAL PEAK POSITION IS I0, AND
; ITS VERTICAL PEAK POSITION IS J0. THE SUBTRACTION IS CARRIED OUT
; SEPARATELY IN EACH QUADRANT SURROUNDING THE CENTER (I0,J0), AND
; THE PARAMETERS DETERMINING THE GAUSSIAN FUNCTION ARE INDEPENDENTLY
; SPECIFIED FOR EACH OF THE QUADRANTS.
;
; CALLING PROTOCOL
;
;       CALL SUBTR(IAC,I1,I2,J1,J2)
;
;       WHERE IAC IS PROPORTIONAL TO THE PEAK AMPLITUDE (SEE PROGRAM
;       SURF6.FOR FOR MORE DETAILS) AND WHERE I1, I2, J1, AND J2 DETERMINE
;       THE AREA IN WHICH A GAUSSIAN FUNCTION IS SUBTRACTED:
;
; I1    THE VERTICAL SUBTRACTION BOUNDARY TO THE LEFT OF I0
; I2    THE VERTICAL SUBTRACTION BOUNDARY TO THE RIGHT OF I0
; J1    THE SUBTRACTION BOUNDARY BELOW J0
; J2    THE SUBTRACTION BOUNDARY ABOVE J0
;
; THESE COORDINATES ARE WITH RESPECT TO THE FACE OF THE VIDEO MONITOR.
; HORIZONTAL POSITION IS DENOTED BY THE VARIABLE I AND VERTICAL POSITION
; BY THE VARIABLE J. THE LOWER LEFT HAND CORNER IS THE ORIGIN (0,0).
;
; THE GAUSSIAN MODEL USED IN EACH QUADRANT IS GIVEN BY
;
; IN THE LOWER LEFT HAND QUADRANT
; WHERE (I .GE. I1 .AND. I .LE. I0 .AND. J .GE. J1 .AND. J .LE. J0)
;
; IA(I,J)=IA0*{ EXP[-{(I-I0)/ISIG1}2] + EXP[-{(J-J0)/JSIG1}2]}
;
; IN THE LOWER RIGHT HAND QUADRANT
; WHERE (I .GT. I0 .AND. I .LE. I2 .AND. J .GE. J1 .AND. J .LE. J0)
;
; IA(I,J)=IA0*{ EXP[-{(I-I0)/ISIG2}2] + EXP[-{(J-J0)/JSIG1}2]}
;
; IN THE UPPER LEFT HAND QUADRANT
; WHERE (I .GE. I1 .AND. I .LE. I0 .AND J .GT. J0 .AND. J .GE. J2)
;
; IA(I,J)=IA0*{ EXP[-{(I-I0)/ISIG1}2] + EXP[-{(J-J0)/JSIG2}2]}
;
; IN THE UPPER RIGHT HAND QUADRANT
; WHERE (I .GT. I0 .AND. I .LE. I2 .AND J .GT. J0 .AND. J .GE. J2)
;
; IA(I,J)=IA0*{ EXP[-{(I-I0)/ISIG2}2] + EXP[-{(J-J0)/JSIG2}2]}
;
; GENERATION OF THE GAUSSIAN MODEL FOR EACH POSITION I,J IS DONE BY
; USING TWO TABLES: A QUADRATIC LOOKUP TABLE AND A LOGARITHMIC
; TRANSFORMATION TABLE. THIS REDUCES PROGRAM EXECUTION TIME
; BECAUSE IT ELIMINATES MULTIPLICATIONS ALTOGETHER. GENERATING EACH
; GAUSSIAN VALUE IA(I,J) USING THE TABLES REQUIRES ONLY TWO ADDITIONS.
; THE ACTUAL VOLUME OF  CH 2D GAUSSIAN FUNCTION   CALCULATED DURING
; ITS GENERATION BECAUSE THE EXACT FORMULA FOR THE VOLUME OF A 2D GAUSSIAN
; MIGHT RESULT IN SIGNIFICANT ERROR. THIS IS TRUE BECAUSE THE GENERATED
; GAUSSIANS DO NOT SPAN THE SAME AREA AS THAT REQUIRED BY THE 2D GAUSSIAN
; FORMULA.
;
; CODE BY J.G. ELIAS, EPL, DUPONT EXP. STATION, JAN-22-1982
;
;
;
; COMMON BLOCK, BLK1, CONTAINS THE BOUNDARIES FOR THE DATA
; ANALYSIS. SEE PROGRAM 'SURF6.FOR' FOR DEFINITIONS.
;
```

```
        .PSECT  BLK1    GBL,D,OVR,RW,REL
ISTART: .BLKW   1
ISTOP:  .BLKW   1
JSTART: .BLKW   1
JSTOP:  .BLKW   1
;
; COMMON BLOCK, BLK4, CONTAINS THE REDUCED VOLUME DATA
; AND THE CALCULATED VOLUME OF THE GENERATED 2D GAUSSIAN
;
        .PSECT  BLK4    GBL,D,OVR,RW,REL
IPRVOL: .BLKW   2
IMRVOL: .BLKW   2
JPRVOL: .BLKW   2
JMRVOL: .BLKW   2
GVOL:   .BLKW   2
;
; COMMON BLOCK, BLK5, CONTAINS THE GAUSSIAN PARAMETERS
; WHICH ARE USED IN SUBTRACTING OUT A TWO DIMENSIONAL
; GAUSSIAN FUNCTION FROM THE DATA.
;
        .PSECT  BLK5    GBL,D,OVR,RW,REL
ISIG1:  .BLKW   1
ISIG2:  .BLKW   1
JSIG1:  .BLKW   1
JSIG2:  .BLKW   1
I0:     .BLKW   1
J0:     .BLKW   1
IA0:    .BLKW   1

;
; COMMON BLOCK, BLK3, CONTAINS THE LOGRITHMIC TRANSFORMATION
; TABLE VALUES AND THE QUADRATIC LOOKUP TABLE VALUES USED TO
; CONSTRUCT A TWO DIMENSIONAL GAUSSIAN WITHOUT MULTIPLICATION.
; SEE PROGRAM 'SURF6.FOR' FOR MORE DETAIL.
;
        .PSECT  BLK3    GBL,D,OVR,RW,REL
IZLOG:  .BLKW   5360            ;THIS IS THE 2800. WORD
                                ;LOG TRANSFORMATION TABLE
IJTAB:  .BLKW   7640            ;THIS IS THE 4000. WORD
                                ;QUADRATIC LOOKUP TABLE
;
        .PSECT  S5
KI:     .WORD   0               ;START OF TEMPORARY
KJ:     .WORD   0               ;STORAGE LOCATIONS
IB1:    .WORD   0               ;
VAR:    .WORD   0               ;
IAC:    .WORD   0               ;
I1:     .WORD   0               ;LEFT STARTING COORDINATE
I2:     .WORD                   ;RIGHT END1   COORDINATE
J1:     .WORD   0               ;BOTTOM STARTING COORDINATE
J2:     .WORD   0               ;TOP ENDING COORDINATE
JEXP:   .WORD   0               ;
IVAR1:  .WORD   0               ;
IVAR2:  .WORD   0               ;
JVAR1:  .WORD   0               ;
LOOP1:  .WORD   0               ;
IMRVL:  .BLKW   2
IPRVL:  .BLKW   2
JVAR2:  .WORD   0               ;
LOOP2:  .WORD   0               ;END OF TEMPRORARY
PIX:    .WORD   0               ;STORAGE LOCATIONS
ROW:    .WORD   0
;
;
        .GLOBL  SUBTR,ZMAXUP,YADDR,XADDR,IMUD
;
SUBTR:  MOV     @2(R5),IAC      ;GET M*ALOG(IA0) VALUE
;
; PICKUP SUBTRACTION LIMITS
;
; LEFT BAND LIMIT, I1
;
```

```
            MOV     @4(R5),I1
;
; RIGHT HAND LIMIT, I2
;
            MOV     @6(R5),I2
;
; BOTTOM LIMIT, J1
;
            MOV     @10(R5),J1
;
; TOP LIMIT, J2
;
            MOV     @12(R5),J2

MOV     R5,-(SP)            ;SAVE ARGUMENT POINTER
;
; CALCULATE THE QUADRATIC LOOKUP TABLE INDEX VALUES. THE
; TABLE IS 4000. WORDS LONG AND REPRESENTS TWO STANDARD
; DEVIATIONS FULL SCALE. SEE PROGRAM 'SURF6.FOR' FOR
; MORE DETAIL ON THE TABLE STRUCTURE.
;
;
; LEFT HAND INDEX, IVAR1
;
            CLR     R0
            MOV     #3721,R1            ;LOAD R1 WITH 2001.
            DIV     ISIG1,R0
            MOV     R0,IVAR1            ;LEFT HAND INDEX
            ASL     IVAR1               ;MULT FOR WORD ADDRESSING
;
; RIGHT HAND INDEX, IVAR2
;
            CLR     R0
            MOV     #3721,R1
            DIV     ISIG2,R0
            MOV     R0,IVAR2            ;RIGHT HAND INDEX
            ASL     IVAR2               ;WORD ADDRESSING
; BOTTOM INDEX, JVAR1
;
            CLR     R0
            MOV     #3721,R1
            DIV     JSIG1,R0
            MOV     R0,JVAR1            ;BOTTOM INDEX
            ASL     JVAR1               ;WORD ADDRESSING
;
; TOP INDEX,JVAR2
;
            CLR     R0
            MOV     #3721,R1
            DIV     JSIG2,R0
            MOV     R0,JVAR2            ;TOP INDEX
            ASL     JVAR2               ;WORD ADDRESSING
;
;
; SETUP FOR SUBTRACTION LOOPS
;
;           LOAD ROW REGISTER
;
            MOV     J1,ROW              ;LOCATION ROW CONTAINS THE
            DEC     ROW                 ;CURRENT ROW NUMBER. ROW MUST
                                        ;BE USED BECAUSE YADDR IS WRITE
                                        ;ONLY
;
;           CALCULATE ROW INDEX
;
            MOV     J0,R1               ;PREPARE INDEX
            SUB     J1,R1               ;COUNTER
            MOV     R1,KJ               ;SAVE ROW LOOP COUNT
            MUL     JVAR1,R1            ;CALCULATE INDEX INCREMENT
            MOV     R1,R4               ;STORE IT
;
;           CALCULATE COLUMN INDEX
;
```

```
;       FOR I1 TO I0
;
        MOV     I0,LOOP1                ;CALCULATE LOOP COUNT
        SUB     I1,LOOP1
        INC     LOOP1
;
;       AND FOR I0+1 TO I2
;
        MOV     I2,LOOP2                ;CALCULATE 2ND LOOP
        SUB     I0,LOOP2
        INC     LOOP2
;
; CALCULATE LOOKUP TABLE INDEX STARTING VALUE
; FOR I1 TO I0 PORTION
;
        MOV     LOOP1,R1                ;GET LOOP COUNT
        DEC     R1
        MUL     IVAR1,R1                ;STARTING VALUE
        MOV     R1,VAR                  ;SAVE IT
;
; START SUBTRACTION OF GAUSSIAN FUNCTION
;
        CLR     IPRVOL                  ;ZERO REDUCED VOLUME
        CLR     IPRVOL+2
        CLR     JPRVOL                  ;ACCUMULATORS
        CLR     JPRVOL+2
        CLR     IMRVOL
        CLR     IMRVOL+2
        CLR     JMRVOL
        CLR     JMRVOL+2
        CLR     IMRVL
        CLR     IMRVL+2
        CLR     IPRVL
        CLR     IPRVL+2
        CLR     PIX
        CLR     GVOL                    ;ZERO GAUSSIAN VOLUME
        CLR     GVOL+2                  ;ACCUMULATOR
;
; J LOOP SUBTRACTION, FROM J1 TO J0
;
10$:    INC     ROW                     ;POINT TO NEXT ROW
                                        ;NOTE: ROW MUST BE USED BECAUSE
                                        ;YADDR IS WRITE ONLY
        MOV     ROW,@#YADDR             ;LOAD YADDR
        MOV     LOOP1,R0                ;COLUMN LOOP COUNTER
        MOV     I1,R2                   ;POINT TO STARTING COLUMN
        ADD     #XADDR,R2               ;ADD OFFSET
        MOV     IAC,R3                  ;STORE M*ALOG(IA0)
        SUB     IJTAB(R4),R3            ;SUB QUADRATIC TABLE VALUE
                                        ;FROM M*ALOG(IA0)
        MOV     R3,R5                   ;& STORE IN R5
        MOV     VAR,R1                  ;GET STARTING LOOKUP TABLE VALUE
        MOV     R4,-(SP)                ;SAVE INDEX INCREMENT
;
;I LOOP SUBTRACTION FROM I1 TO I0
;
12$:    MOV     R5,R3                   ;MOV M*ALOG(IA0)-QUADR. TABLE
                                        ;VALUE INTO R3
        SUB     IJTAB(R1),R3            ;SUB QUADRATIC TABLE VALUE FROM
                                        ;M*ALOG(IA0)-((J-J0)/SIG)**2
        ASL     R3                      ;SET FOR WORD ADDRESSING
        ;
        ; NOTE: R4 IS USED BELOW TO STORE THE PIXEL VALUE
        ;       BECAUSE THE EPL MEMORY IS ONLY 8 BITS/PIXEL
        ;       IN THIS IMPLEMENTATION (1024 X 1024) AND
        ;       WOULD NOT INDICATE NEGATIVE VALUES UPON
        ;       SUBTRACTION. WITH SIGNED MEMORY R4 CAN BE
        ;       ELIMINATED THUS INCREASING COMPUTING SPEED.
        ;       PIX IS USED TO AVOID SIGN EXTENSION IN MOVB
        ;       TO REGISTER INSTRUCTION.
```

```
        MOVB    @R2,PIX                 ;GET IMAGE DATA VALUE
        MOV     PIX,R4                  ;
        ADD     IZLOG(R3),GVOL          ;ACCUMULATE GENERATED GAUSSIAN
        ADC     GVOL+2                  ;VOLUME
        SUB     IZLOG(R3),R4            ;SUBTRACT TRANSFORMED PIXEL
                                        ;VALUE FROM IMAGE DATA
        BPL     14$                     ;BR IF IMAGE DATUM>0
        NEG     R4                      ;INVERT SIGN
        ADD     R4,IMRVOL               ;OTHERWISE SAVE REDUCED VOLUME
        ADC     IMRVOL+2
        CLR     R4                      ;AND ZERO PIXEL
14$:    MOVB    R4,(R2)+                ;STORE NEW PIXEL VALUE
        SUB     IVAR1,R1                ;CALCULATE INDEX FOR LOOKUP
        SOB     R0,12$                  ;LOOP THRU COLUMNS
;
; I LOOP SUBTRACTION FROM I0+1 TO I2
;
        MOV     LOOP2,R0                ;LOAD INDEX COUNTER
        CLR     R1
16$:    ADD     IVAR2,R1                ;LOAD LOOKUP TABLE
                                        ;VALUE
        MOV     R5,R3                   ;RELOAD
        SUB     IJTAB(R1),R3            ;SUB QUADR. TABLE VALUE
        ASL     R3
;
; SEE ABOVE R4 AND PIX NOTE
;
        MOVB    @R2,PIX                 ;GET DATA
        MOV     PIX,R4
        ADD     IZLOG(R3),GVOL
        ADC     GVOL+2
        SUB     IZLOG(R3),R4            ;SUB TRANSFORMATION PIXEL
                                        ;VALUE FROM IMAGE
        BPL     18$
        NEG     R4                      ;INVERT SIGN
        ADD     R4,IPRVOL               ;STORE REDUCED VOLUME
        ADC     IPRVOL+2
        CLR     R4
18$:    MOVB    R4,(R2)+                ;STORE NEW PIXEL VALUE
        SOB     R0,16$
;
;
        MOV     ROW,R4                  ;LOAD CURRENT ROW #
        CALL    ZMAXUP                  ;UPDATE LINE
        MOV     ROW,R4
        CALL    IMUD                    ;UPDATE VIDEO DISPLAY
        MOV     (SP)+,R4                ;GET INDEX VALUE
19$:    SUB     JVAR1,R4
        DEC     KJ                      ;LOOP THRU ROWS
        BPL     10$
;
; THIS PART SAVES THE REDUCED VOLUME THAT WAS ACCUMULATED IN THE
; LOWER HALF OF THE SUBTRACTION AREA, i.e. the area from J1 to J0
; between I1 and I2
;
        MOV     IPRVOL,JMRVOL           ;GET LOW WORD IN IPRVOL
        MOV     IPRVOL+2,JMRVOL+2       ;GET UPPER WORD IN IPRVOL
        ADD     IMRVOL,JMRVOL           ;ADD LOW WORD IN IMRVOL
        ADC     JMRVOL+2
        ADD     IMRVOL+2,JMRVOL+2       ;ADD UPPER WORD IN IMRVOL
;
;
; J SUBTRACTION LOOP, J0+1 TO J2
;
        MOV     J2,R1                   ;CALC. LOOP COUNTER
        SUB     J0,R1
        DEC     R1
        MOV     R1,KJ                   ;STORE IT
        CLR     PIX
        CLR     R4
```

```
;
20$:    INC     ROW                     ;POINT TO NEXT ROW
        MOV     ROW,@#YADDR             ;LOAD NEW ROW NUMBER
        MOV     LOOP1,R0                ;COLUMN LOOP COUNTER
        MOV     I1,R2                   ;POINT TO STARTING COLUMN
        ADD     #XADDR,                 ;ADD OFFSE.
        ADD     JVAR2,R4                ;CALC. INDEX FOR LOOKUP TABLE
        MOV     IAC,R3                  ;STORE M*ALOG(IA0)
        SUB     IJTAB(R4),R3            ;SUB QUADRATIC TABLE VALUE
                                        ;FROM M*ALOG(IA0)
        MOV     R3,R5                   ;& STORE IN R5
        MOV     VAR,R1                  ;GET STARTING LOOKUP TABLE VALUE
        MOV     R4,-(SP)                ;SAVE INDEX VALUE
;
; I LOOP SUBTRACTION, FROM I1 TO I0
;
22$:    MOV     R5,R3                   ;MOV M*ALOG(IA0)-QUADR. TABLE
                                        ;VALUE INTO R3
        SUB     IJTAB(R1),R3            ;SUB QUADRATIC TABLE VALUE FROM
                                        ;M*ALOG(IA0)-((J-J0)/SIG)**2
        ASL     R3                      ;SET FOR WORD ADDRESSING
;
; SEE ABOVE R4 AND PIX NOTE
;
        MOVB    @R2,PIX                 ;GET DATA
        MOV     PIX,R4
        ADD     IZLOG(R3),GVOL          ;ACCUMULATE GENERATED GAUSSIAN
        ADC     GVOL+2                  ;VOLUME
        SUB     IZLOG(R3),R4            ;SUBTRACT TRANSFORMED PIXEL
                                        ;VALUE FROM IMAGE DATA
        BPL     24$                     ;BR IF IMAGE DATUM>0
        NEG     R4                      ;INVERT SIGN
        ADD     R4,IMRVL                ;OTHERWISE STORE REDUCED VOLUME
        ADC     IMRVL+2
        CLR     R4                      ;AND ZERO PIXEL
24$:    MOVB    R4,(R2)+                ;STORE NEW PIXEL VALUE
        SUB     IVAR1,R1                ;CALCULATE INDEX FOR LOOKUP
        SOB     R0,22$                  ;LOOP THRU COLUMNS
;
; I LOOP SUBTRACTION FROM I0+1 TO I2
;
        MOV     LOOP2,R0                ;LOAD INDEX COUNTER
        CLR     R1
26$:    ADD     IVAR2,R1                ;LOAD LOOKUP TABLE
                                        ;VALUE
        MOV     R5,R3                   ;RELOAD
        SUB     IJTAB(R1),R3            ;SUB QUADR. TABLE VALUE
        ASL     R3
;
; SEE ABOVE R4 AND PIX NOTE
;
        MOVB    @R2,PIX                 ;GET DATA
        MOV     PIX,R4
        ADD     IZLOG(R3),GVOL          ;STORE GENERATED GAUSSIAN
        ADC     GVOL+2                  ;VOLUME
        SUB     IZLOG(R3),R4            ;SUB TRANSFORMATION PIXEL
                                        ;VALUE FROM IMAGE
        BPL     28$
        NEG     R4                      ;INVERT SIGN
        ADD     R4,IPRVL                ;STORE REDUCED VOLUME
        ADC     IPRVL+2
        CLR     R4
28$:    MOVB    R4,(R2)+                ;STORE NEW PIXEL VALUE
        SOB     R0,26$
;
;
        MOV     ROW,R4                  ;LOAD CURRENT ROW #
        CALL    ZMAXUP                  ;UPDATE LINE
        MOV     ROW,R4
        CALL    IMUD                    ;UPDATE VIDEO DISPLAY
        MOV     (SP)+,R4
;
29$:    DEC     KJ                      ;LOOP THRU ROWS
        BPL     20$
```

```
;
; THIS PART SAVES THE REDUCED VOLUME THAT WAS ACCUMULATED IN THE
; UPPER HALF OF THE SUBTRACTION AREA, i.e. the area from J0+1 to
; J2 between I1 and I2.
;
        MOV     IMRVL,JPRVOL            ;GET LOW WORD IN IMRVL
        MOV     IMRVL+2,JPRVOL+2        ;GET UPPER WORD IN IMRVL
        ADD     IPRVL,JPRVOL            ;ADD LOW WORD IN IPRVL
        ADC     JPRVOL+2
        ADD     IPRVL+2,JPRVOL+2        ;ADD UPPER WORD IN IPRVL
;
;
        ADD     IMRVL,IMRVOL
        ADC     IMRVOL+2
        ADD     IMRVL+2,IMRVOL+2
        ADD     IPRVL,IPRVOL
        ADC     IPRVOL+2
        ADD     IPRVL+2,IPRVOL+2
;
        MOV     (SP)+,R5                ;POP ARG POINTER
;
40$:    RETURN
        .END
```

What is claimed:

1. A method of quantitating spatially integrated intensities of individual spots contained in a multiple spot image defined by a discrete pixel-by-pixel representation of the intensities, which establishes a first sense, of the spots comprising the steps of:
   (a) searching the image for the pixel representing the greatest intensity deviation in the first sense from a reference intensity level,
   (b) constructing a mathematical three dimensional model of the spot containing such pixel, one of the dimensions being related to spot intensity,
   (c) compensating the image by subtracting the mathematical model therefrom leaving possible overcompensated regions in the image which; regions together constitute a reduction volume,
   (d) adjusting the dimensions of the model by the amount necessary to give the model the same volume as the volume removed from the image in step (c) less the reduction volume,
   (e) restoring all such overcompensated regions to the reference intensity level,
   (f) quantitating the spot from the adjusted model by determining the volume of the adjusted model by multiplying the model's dimensions together and
   (g) repeating steps (a) through (f) for successive pixels each having a lower intensity deviation from the reference level until the image is of substantially constant intensity.

2. The method set forth in claim 1 wherein the mathematical model is a Gaussian model.

3. The method set forth in claim 1 wherein the model step (b) is formed by least squares curve fitting.

4. The method set forth in claim 1 wherein the model of step (b) is defined by searching the image in four orthogonal directions from the greatest deviation pixel to ascertain the length and width of the spot along each direction.

5. The method set forth in claim 4 wherein the model of step (b) is formed to be an asymmetric function of position relative to the greatest deviation pixel.

6. The method set forth in claim 5 wherein the model of step (b) is formed by at least squares curve fitting.

7. The method set forth in claim 5 wherein mdels formed in step (b) of adjacent pixels are combined to form composite models of each individual spot.

8. The method set forth in claim 7 which includes the additional steps of quantitating the spot to obtain its center of mass by obtaining the center of mass of the model, adjusting the location of the model for the step (a) pixel according to the alteration of the center of mass caused by the removal of the reduction volume by determining the center of mass of the reduction volume, combining these results to obtain the center of mass of the difference, and placing the adjusted model of step (d) at the center of mass of the difference.

9. The method set forth in claim 8 which includes the additional step of determining the extent of the composite model by combining component model moments of inertia according to the parallel axis theorem.

10. The method according to claim 9 wherein the model of step (b) is defined by searching the image in four orthogonal directions from the greatest deviation pixel to ascertain the length and width of the spot along each direction.

11. The method according to claim 7 wherein the model of step (b) is defined by searching the image in four orthogonal directions from the greatest deviation pixel to ascertain the length and width of the spot along each direction.

12. The method set forth in claim 4 wherein models formed in step (b) of adjacent pixels are combined to form composite models of each individual spot.

13. The method set forth in claim 4 which includes the additional steps of
   quantitating the spot to obtain its center of mass by obtaining the center of mass of the model, and
   adjusting the location of the model for the step (a) pixel according to the alteration of the center of mass caused by the removal of the reduction volume by determining the center of mass of the reduction volume, combining these results to obtain the center of mass of the difference, and placing the adjusted model of step (d) at the center of mass of the difference.

14. The method set forth in claim 4 wherein the model of step (b) is defined by searching the image in four orthogonal directions from the greatest deviation pixel to ascertain the length and width of the spot along each direction.

15. The method set forth in claim 1 wherein models formed in step (b) of adjacent pixels are combined to form composite models of each individual spot.

16. The method set forth in claim 1 which includes the additional steps of quantitating spatially integrated intensities of individual spots contained in a multiple spot image defined by a discrete pixel-by-pixel representation of the intensity of the spots which includes the additional steps of quantitating the spot to obtain its center of mass, adjusting the location of the model for the step (a) pixel according to the alteration of the center of mass caused by the removal of the reduction volume.

17. The method according to claim 1 which includes the additional steps of:
    quantitating the adjusted model to obtain its moment of inertia, and
    determining the extent of the adjusted model by combining the moments of inertia of the model and its reduction volume according to the parallel axis theorem.

18. In a system for quantitating individual spots contained in a multiple spot image defined by a discrete pixel-by-pixel representation of the intensity of the spots, the system including a memory for storing the pixels, means for determining that pixel representing the greatest intensity deviation from a reference intensity level, and means for constructing a mathematical three-dimensional model of the spot containing such pixel, one of the dimensions being related to spot intensity, the improvement which includes:
    means for compensating the image by subtracting the mathematical model therefrom leaving possible overcompensated regions in the stored image which regions together constitute a reduction volume,
    means for adjusting the dimensions of the model by the amount necessary to give the model the same volume as the volume removed from the image in step (c) less the reduction volume, restoring all such overcompensated regions to the reference intensity level,
    means for quantitating the spot from the adjusted model by determining the volume of the adjusted model by multiplying the model's dimension.

* * * * *